US007638328B2

(12) United States Patent
Eriksson et al.

(10) Patent No.: US 7,638,328 B2
(45) Date of Patent: Dec. 29, 2009

(54) METHOD FOR EFFICIENT TRANSFER OF HUMAN BLASTOCYST-DERIVED STEM CELLS (HBS CELLS) FROM A FEEDER-SUPPORTED TO A FEEDER-FREE CULTURE SYSTEM, LONG-TERM PROPAGATION OF HBS CELLS UNDER FEEDER-FREE CONDITIONS AND USE OF CULTURED HBS CELLS FOR APPLICATIONS IN MYOCARDIAL REGENERATION

(75) Inventors: Peter Eriksson, Gothenburg (SE); Eva Karin Kilmare, Gothenburg (SE); Tommi Tallheden, Gothenburg (SE); Sven Enerbäck, Gothenburg (SE)

(73) Assignee: Cellartis AB, Göteborg (SE)

( * ) Notice: Subject to any disclaimer, the term of this patent is extended or adjusted under 35 U.S.C. 154(b) by 293 days.

(21) Appl. No.: 10/555,694

(22) PCT Filed: May 10, 2004

(86) PCT No.: PCT/EP2004/005033

§ 371 (c)(1),
(2), (4) Date: Nov. 4, 2005

(87) PCT Pub. No.: WO2004/099394

PCT Pub. Date: Nov. 18, 2004

(65) Prior Publication Data

US 2007/0010010 A1 Jan. 11, 2007

Related U.S. Application Data

(60) Provisional application No. 60/469,320, filed on May 8, 2003.

(30) Foreign Application Priority Data

May 8, 2003 (DK) ............................... 2003 00700
Jun. 27, 2003 (DK) ............................... 2003 00983

(51) Int. Cl.
C12N 5/08 (2006.01)
C12N 5/00 (2006.01)
C12N 5/02 (2006.01)
(52) U.S. Cl. ...................... 435/366; 435/375; 435/377; 435/378; 435/379; 435/395
(58) Field of Classification Search ................. 435/366, 435/325, 374, 379, 378, 375, 395
See application file for complete search history.

(56) References Cited

U.S. PATENT DOCUMENTS

| 6,200,806 B1 | 3/2001 | Thomson |
| 2002/0164308 A1 | 11/2002 | Reubinoff et al. |
| 2003/0083497 A1* | 5/2003 | Bouchard et al. ............ 544/405 |

FOREIGN PATENT DOCUMENTS

| WO | 97/20035 A1 | 6/1997 |
| WO | 01/83715 A2 | 11/2001 |
| WO | 02/059278 A2 | 8/2002 |
| WO | 02/086107 A2 | 10/2002 |
| WO | 02/092756 A2 | 11/2002 |
| WO | 03/029443 A1 | 4/2003 |
| WO | 03/029445 A1 | 4/2003 |
| WO | 03/050249 A2 | 6/2003 |
| WO | 03/055992 A2 | 7/2003 |
| WO | 03/062405 A2 | 7/2003 |

OTHER PUBLICATIONS

Roach and McNeish (Methods in Molecular Biology, 185: Embryonic Stem Cells: Methods and Protocols. Edited by K. Turksen, Human Press, Inc., Totowa, NJ, 2002, pp. 1-16.*
Amit, M et al, 2004, Feeder-layer and serum-free culture of human embryonic stem cells, Biology of Reproduction, 70:837-845.*
Draper, JS et al., 2004, Culture and Characterization of Human Embryonic Stem Cells, Stem Cells and Development, 13:325-336.*
Thomson, JA et al. , 1995, Isolation of a primate embryonic stem cell line, PNAS, 92:7844-7848.*
Okabe, Shigeo, et al.; "Development of Neuronal Precursor Cells and Functional Postmitotic Neurons From Embryonic Stem Cells in Vitro"; Mechanisms of Development; 1996; pp. 89-102; vol. 59; Elsevier Science Ireland Ltd.
Gardner, David K., et al.; "Fetal Development After Transfer is Increased by Replacing Protein with the Glycosaminoglycan Hyaluronan for Mouse Embryo Culture and Transfer"; Human Reproduction; 1999; pp. 2572-2580; vol. 14, No. 10; European Society of Human Reproduction and Embryology.
Gardner, David K. et al.; "Physiology and Culture of the Human Blastocyst"; Journal of Reproductive Immunology; 2002; pp. 85-100; vol. 55; Elsevier Science Ireland Ltd.
Xu, Chunhui et al.; "Feeder-Free Growth of Undifferentiated Human Embryonic Stem Cells"; Nature Biotechnology; Oct. 2001; pp. 971-974; vol. 19; Nature Publishing Group.
Gepstein, Lior; "Derivation and Potential Applications of Human Embryonic Stem Cells"; Circulation Research; Nov. 15, 2002; pp. 866-876.

(Continued)

Primary Examiner—Valarie Bertoglio
(74) Attorney, Agent, or Firm—Buchanan Ingersoll & Rooney PC

(57) ABSTRACT

A method for the transfer of human blastocyst-derived stem cells (hBS cells) to feeder-free culture system and propagation of the cells in such a feeder-free culture system, the method comprising the following steps of (a) transferring the balstocyst-derived stem cells from feeder to feeder free culture by mechanical treatment, (b) optionally, culturing the blastocyst-derived stem cells under feeder cell free growth conditions in a suitable growth medium and/or on a suitable support substrate, and (c) optionally passaging the blastocyst derived stem cell line every 3-10 days by enzymatic and/or mechanical treatment. The invention also relates to the application of hBS cells cultured under feeder free condition in medicine (e.g., myocardial regeneration) and screening and toxicity tests.

20 Claims, 15 Drawing Sheets

OTHER PUBLICATIONS

Figure 1:
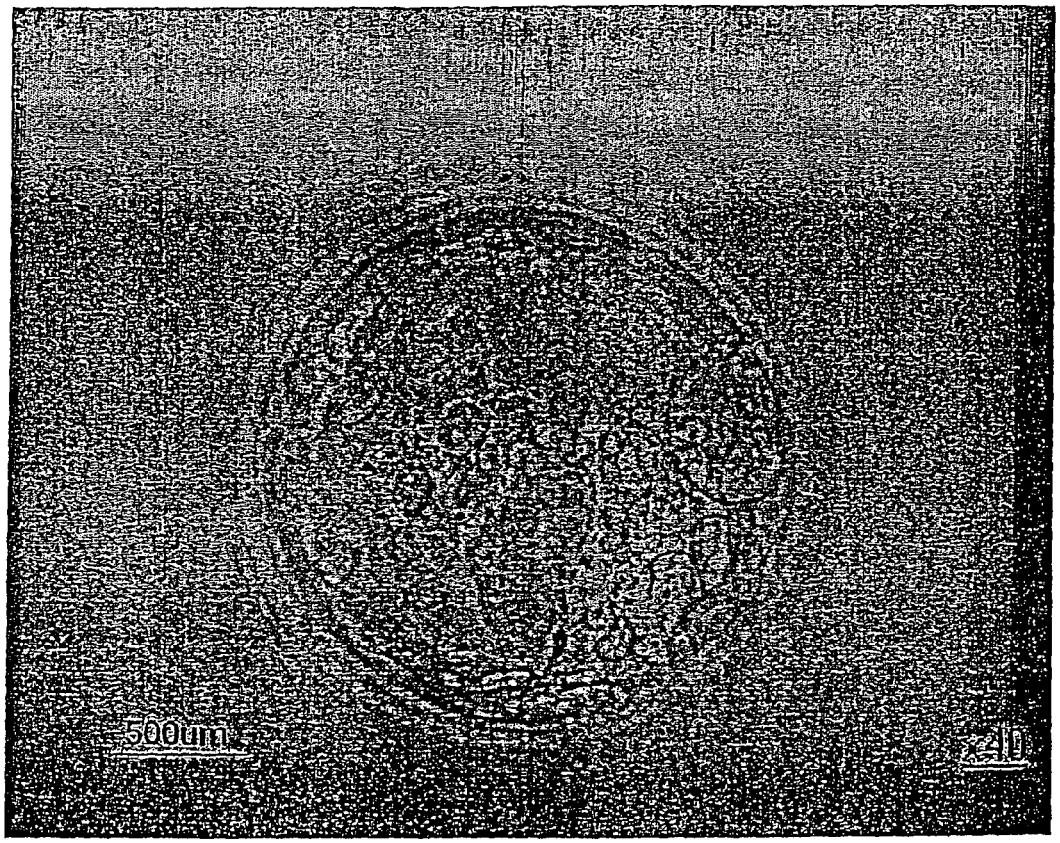

Ropeter-Scharfenstein, M., et al.; "Identification, Isolation and Culture of Pluripotent Cells From the Porcine Inner Cell Mass"; Journal of Animal Breeding and Genetics; 1996; pp. 427-436; vol. 113.

Lumelsky, Nadya, et al.; "Differentiation of Embryonic Stem Cells to Insulin-Secreting Structures Similar to Pancreatic Islets"; Science; May 18, 2001; pp. 1389-1394; vol. 292.

Thomson, James A., et al., "Embryonic Stem Cell Lines Derived from Human Blastocysts", Science, Nov. 6, 1998, pp. 1145-1147, vol. 282.

English Translation of Japanese Office Action.

Klimanskya et al., "Human Embryonic Stem Cell Lines Derived from Single Blastomeres", Nature (2006) vol. 444, No. 23, pp. 481-485.

Nakatsuji, "Human Pluripotent Stem Cell Lines (ES-EG Cell Line)", Regenerative Medicine and Life Sciences: Reproduction Technology, Stem Cell Technology and Tissue Engineering, vol. 45, No. 13, pp. 2040-2046 (with English Language Translation).

* cited by examiner

Mitotic index:

| Culture method | Mean | Std. dev. |
|---|---|---|
| Feeder (mEF) | 4.19 | 0.939 |
| Feeder-free (Matrigel™) | 3.50 | 0.655 |

Fig 13

METHOD FOR EFFICIENT TRANSFER OF HUMAN BLASTOCYST-DERIVED STEM CELLS (HBS CELLS) FROM A FEEDER-SUPPORTED TO A FEEDER-FREE CULTURE SYSTEM, LONG-TERM PROPAGATION OF HBS CELLS UNDER FEEDER-FREE CONDITIONS AND USE OF CULTURED HBS CELLS FOR APPLICATIONS IN MYOCARDIAL REGENERATION

This instant application is a 371 of PCT/EP04/05033, filed May 10, 2004, which claims benefit of U.S. Provisional Application 60/469,320, filed May 8, 2003.

The benefit is claimed under 35 U.S.C. §119(a)-(d) of Danish Patent Application No. PA 2003 00700, filed May 8, 2003, and Danish Patent Application No. PA 2003 00983, filed Jun. 27, 2003.

FIELD OF THE INVENTION

The present invention concerns a method for the transfer of human blastocyst-derived stem cells (hBS cells) to feeder-free culture system and propagation of the cells in such a feeder-free culture system. The invention also relates to the application of hBS cells cultured under feeder free condition in myocardial regeneration.

BACKGROUND OF THE INVENTION

A stem cell is a cell type that has a unique capacity to renew itself and to give rise to specialized or differentiated cells. Although most cells of the body, such as heart cells or skin cells, are committed to conduct a specific function, a stem cell is uncommitted, until it receives a signal to develop into a specialized cell type. What makes the stem cells unique is their proliferative capacity, combined with their ability to become specialized. For years, researchers have focused on finding ways to use stem cells to replace cells and tissues that are damaged or diseased. So far, most research has focused on two types of stem cells, embryonic and somatic stem cells. Embryonic stem cells are derived from the preimplanted fertilized oocyte, i.e. blastocyst, whereas the somatic stem cells are present in the adult organism, e.g. within the bone marrow, epidermis and intestine. Pluripotency tests have shown that whereas the embryonic or blastocyst-derived stem cells (hereafter referred to as blastocyst-derived stem cells or (BS cells) can give rise to all cells in the organism, including the germ cells, somatic stem cells have a more limited repertoire in descendent cell types.

In 1998, investigators were for the first time able to isolate hBS cells from human fertilized oocytes and to grow them in culture see e.g. U.S. Pat. No. 5,843,780 and in U.S. Pat. No. 6,200,806.

The procedure used in the patent specifications mentioned above depends on the use of blastocysts with an intact zona pellucida. Furthermore, the method disclosed in these patents specifically use inner cell mass cells that have been isolated by iminunosurgery for plating on mouse embryonic feeder cells. This method has several drawbacks, for example, it is time consuming, technically difficult and results in low yields of stem cells. Taken together, these drawbacks make it a costly method.

The so far few publications in the field illustrate the problems associated with establishing these stein cells from human blastocysts. As a result very few hBS cell lines are available.

Perhaps the most far-reaching potential application of hBS cells is the generation of cells and tissue that could be used for so-called cell therapies. Many diseases and disorders result from disruption of cellular function or destruction of tissues of the body. Today, donated organs and tissues are often used to replace ailing or destroyed tissue. Unfortunately, the number of people suffering from disorders suitable for treatment by these methods far outstrips the number of organs available for transplantation. The availability of hBS cells and the intense research on developing efficient methods for guiding these cells towards different cell fates, e.g. insulin-producing β-cells, cardiomnyocytes, and dopamine-producing neurons, holds growing promise for future applications in cell-based treatment of degenerative diseases, such as diabetes, myocardial infarction and Parldnson's.

A significant challenge to the use of pluripotent stem cells for therapy is that they are traditionally cultured on a layer of feeder cells to prevent differentiation and to promote cell survival and proliferation. Without feeder cells in the culture environment, the stein cells will die, or differentiate into a heterogeneous population of committed cells. Unfortunately, using feeder cells increases production costs, impairs scale-up, and produces mixed cell populations that require the pluripotent stem cells to be separated from feeder cell components. Furthermore, for therapeutic applications it will be of greatest importance that the hBS cells are cultured without xenogenic tissue contact, such as, e.g. feeder cells. Thus, there is a need for developing methods for propagating human blastocyst-derived stem cell lines without the use of feeder cells.

Other potential applications of hBS cells themselves and cell populations derived there from are found e.g. in the drug discovery process in the pharmaceutical industry and in toxicity testings of all kinds of chemicals. Today, large-scale and high throughput screening of drug candidates usually relies on biochemical assays that provide information on compound binding affinity and specificity, but little or no information on function. Functional screening relies upon cell-based screens and usually uses organisms of poor clinical relevance such as bacteria or yeasts that can be produced cheaply and quickly at high volume. Successive rounds of screening use model species of greater clinical relevance, but these are more costly and the screening process is time consuming. Screening tools based on human primary cells or immortalised cell types exist, but these cells are limited in supply or usefulness due to loss of vital functions as a result of in vitro culture and transformation. The access to undifferentiated hBS cells and hBS cells differentiated under engineered conditions and in the absence of interfering feeder cells provides a new and unique capability to conduct human cell-based assays with high capacity, but without compromising clinical relevance.

The following definitions and abbreviations are used herein

DEFINITIONS AND ABBREVIATIONS

As used herein, the term "blastocyst-derived stem cell" is denoted BS cell, and the human form is termed "hBS cells".

As used herein, the term "EF cells" means "embryonic fibroblast cells". These cells could be derived from any mammal, such as mouse or human.

A "conditioned medium" is prepared by culturing EF cells or other fibroblasts in a medium, and then harvesting and filtering the medium.

By the terms "feeder cells" or "feeders" are intended to mean cells of one type that are co-cultured with cells of another type, to provide an environment in which the cells of the second type can grow. The feeder cells may optionally be from a different species as the cells they are supporting. The feeder cells may typically be mitotically inactivated when being co-cultured with other cells by irradiation or treatment with an anti-mitotic agent such as mitomycin c, to prevent them from outgrowing the cells they are supporting.

By the terms "feeder-free culture system", "feeder cell free" or "feeder free" is intended to mean cultures or cell populations wherein less than 10% of the total cells in the culture are feeder cells, such as, e.g., less than 5%, less that 4%, less than 3%, less than 2%, less than 1%, less than 0.5%, less than 0.1% and less than 0.01%. It will be recognized that if a previous culture containing feeder cells is used as a source of hBS cells for the culture to which fresh feeders are not added, there will be some feeder cells that survive the passage. However, after the passage the feeder cells will not proliferate, and only a very small proportion will be viable in continuous cultures.

DESCRIPTION OF THE INVENTION

The inventors have established a novel method for the transfer of hBS cells such as, e.g., a pluripotent human blastocyst-derived stem cell line from a fertilized oocyte to a feeder-free culture system and then propagating the cells in an undifferentiated state. The propagation is also performed under feeder free growth conditions.

According to many national laws in Europe and other countries, a fertilized oocyte is not regarded as an embryo before implantation in the uterus i.e. 10-14 days after fertilization. As the stem cell lines of the present invention are derived from a 4-5-days-old fertilized oocyte, the stem cell lines should therefore not be regarded as an embryonic stem cell line. The right nomenclature of the stem cell lines of the present invention is blastocyst-derived stem cells. Furthermore, the stem cell lines of the present invention are not intended to use for human cloning and the creation of transgenic animals. The present invention does not concern a method to genetically modify the stem cell lines.

The human blastocyst-derived cells suitable for use in a method of the invention are derived from a group of cells called the inner cell mass, which is a part of the blastocyst. A blastocyst is a 4-5 days old fertilized oocyte, which only upon implantation in the uterus can develop to an embryo. Once removed from the blastocyst, the cells of the inner cell mass can be cultured into blastocyst-derived stem cells. The blastocyst-derived stem cells are not intended to develop into embryos.

In a previous patent application published as WO 03/055992 (to the same Applicant) a method for establishing hBS cells is described. Although it is contemplated that in the future it may be possible to establish such cells without use of feeder cells, the current methods available use feeder cells. However, future replacement therapies involving hBS cells or tissues will require that the cells and tissues are produced without contact with any animal (e.g. non-human) sources. Furthermore, the use of hBS cells also relies on the availability of routine large-scale culturing protocols for undifferentiated hBS cells. The present invention addresses this issue by providing a suitable method for transferring hBS cells from a feeder culture system to a feeder-free culture system. hBS cells can be derived from the inner cell mass of the developing blastocyst and maintained undifferentiated for an extended period of passages while retaining stable karyotype and phenotype. hBS cells have the capacity to differentiate into cells and tissues of all three germ layers, both in vivo and in vitro, and are thus said to be pluritpotent. The unique properties of hBS cells suggest that they may supply an almost unlimited source of cells for future replacement therapies, functional genomics and proteomics as well as drug screening.

Mouse BS cells can be cultured without feeder cells if the medium is supplemented with leukaemia inhibitory factor (LIF). However, in cultures of hBS cells, LIF does not have this effect. Today the derivation of hBS cell lines requires either human or mouse blastocyst fibroblast feeders for co-culturing. Protocols for the transfer and propagation of hBS cultures from feeder to feeder-free conditions have previously been described. These feeder-free culture protocols had limitations concerning scale-up properties, low success rate in the initial transfer of the hBS cells from feeder culturing to feeder-free conditions as well as generating a mixed population of undifferentiated and differentiated hBS cells in the cultures.

The present invention provides an optimized method for transfer of hBS cells to a feeder-free culture system, which method is advantageous compared to the known methods in that the cells transferred are stable for at least up to 10 passages. Studies by Richards et al. showed that the hBS cell lines could not be propagated in an undifferentiated state for more than six passages on cell-free matrixes, including MATRIGEL™ (BD Biosciences, San Jose, Calif. USA) (Matrigel™ is a solubilized basement membrane preparation extracted from Engelbreth-Holm-Swann (EHS) mouse sarcoma, a tumor rich in ECM proteins. Its major component is laminin, followed by collagen IV, heparan sulfate proteoglycan, and entactin. (BD Biosciences, Technical Bulletin #455)

However, the present inventors have found that the hBS cells were stable for up to 35 passages on MATRIGEL™, still expressing the markers for undifferentiated hBS cells, even after a cycle of freezing/thawing and growth rates remained roughly comparable. Furthermore, a significantly higher number of surviving colonies were observed two days after plating, when mechanical dissociation was compared with enzymatic dissociation. A critical step seems to bee the initial step for transfer of the hBS cells to a feeder-free culture system. Accordingly, the present invention provides a method for transfer of hBS cells to a feeder-free culture system, wherein the hBS cells are mechanically cut from the feeder. In the examples herein, only the centre part of each colony was used, whereas in previous work by Xu et al., the whole colonies were detached by enzymatic treatment with the risk of contaminating the cultures with feeder cells. Furthermore, the use of enzymes, at the very delicate step of transferring the feeder cultured hBS cells to a feeder-free surface, may cause inactivation of important surface molecules involved in cell adhesion and growth. The major components in MATRIGEL™ are extracellular matrix proteins, like collagen type IV and laminin. Activation of the cell surface integrins upon binding to extracellular matrix proteins is believed to be a crucial step for the regulation of cell adhesion, survival and proliferation. For example, Integrin alpha 1 has a unique role among the collagen receptors in regulating both in vivo and in vitro cell proliferation in collagenous matrices. Laminin-specific receptors, possibly formed by Integrin $\alpha$ 6 and $\alpha$ 1 which are highly expressed by hBS cells, may also play a major role in the adhesion of hBS cell to the matrix surface. Thus, one possibility is that some of the important surface receptors for attachment or survival might be negatively affected by the rough initial collagenase IV treatment before the cells have adapted to the new surface.

In the examples herein different techniques for the transfer of hBS cells to a feeder-free environment were investigated, either by mechanical or enzymatic dissociation, in regards to cell adhesion, survival rate and proliferation. Furthermore, method according to the invention was developed in order to facilitate long-term propagation and large-scale production of homogenous populations of undifferentiated hBS cells. The use of conventional cryopreservation techniques for freezing/thawing of the hBS cells was also examined.

Transfer of hBS Cells to Feeder Free Propagation

Subsequent to dissection of the inner cell mass, the inner cell mass cells are co-cultured with feeder cells to obtain a blastocyst-derived stem (hBS) cell line. After obtaining the hBS cell line, the cell line is optionally propagated to expand the amount of cells. Before propagation of the hBS cells in a feeder-free system, the hBS cells may be transferred to a feeder-free system.

As mentioned herein and further demonstrated in the Examples a critical factor for the success in the propagation of the hBS cells is the method by which the hBS cells is transferred from a feeder culture system to a feeder-free culture system. Accordingly, the hBS cells must be transferred to the feeder-free culture system by mechanical dissection, which may be performed by using a sterile sharpened glass capillary, with a 25 degree angle and a 200 or 300 micrometer lumen, designed for cutting, manipulation, and transfer of hBS colonies, or parts of hBS colonies. It is produced by Swemed Lab International AB, Billdal, Sweden.

As shown in the examples herein, mechanical dissociation resulted in a much more efficient attachment of cells to the MATRIGEL™, a more rapid proliferation compared to the enzyme treated cultures, and the cells were much more stable during passages. Accordingly, the method for transferring the hBS cells according to the invention does not require any enzymatic treatment. As seen in the examples herein, the cells cultured and proliferated under feeder-free conditions have a mitotic index that was similar to that of cells grown under feeder conditions.

The propagation of the blastocyst-derived stem cell line comprises culturing the stem cells under feeder cell free growth conditions, as culturing the hBS cells without feeder cells has a number of advantages, such as, e.g. there is no need for the ongoing production of feeder cells, the production of hBS cells may be easier to scale up and there is no risk of DNA transfer or other infection risks from the feeder cells. If the medium is not correctly conditioned it may infect the new cell line.

Thus, the transfer and propagation step under feeder free conditions may comprise the following steps of
 a. transferring the blastocyst-derived stem cells from feeder to feeder free culture by mechanical treatment.
 b. optionally, culturing the blastocyst-derived stem cells under feeder cell free growth conditions in a suitable growth medium and/or on a suitable support substrate, and
 c. optionally, passaging the blastocyst derived stem cell line every 3-10 days by enzymatic and/or mechanical treatment.

In specific embodiments of the invention all steps i)-iii) are included.

Transfer of hBS Cells from a Feeder Culture System to a Feeder-Free Culture System The transfer step has been found to be a critical step as mentioned above. Accordingly, the transfer should be done by means of mechanically dissociation or mechanical dissection of the cells in the feeder culture system. This mechanical treatment may be done by means of any suitable cutting tool such as a tool having a sharpened end and a size that is appropriate for the cutting. The tool may be made of any suitable material such as, e.g., plastic or glass and an example of a suitable tool is a cutting tool that is a sterile sharpened glass capillary, with a 25 degree angle and a 200 or 300 micrometer lumen, designed for cutting, manipulation, and transfer of hBS cell colonies, or parts of hBS cell colonies. It is produced by Swemed Lab International AB, Billdal, Sweden. In a specific embodiment the hBS cells to be transferred is a colony of hBS cells and pieces is cut from the centre of the colony and suspended in a suitable medium as cell clusters. The cell clusters are dissociated mechanically one or more times e.g. until the cell clusters have a size that is at least 50% such as, e.g., at the most about 40%, at the most about 30%, at the most about 20%, at the most about 10% or at the most about 5% of that of the original colony. The size is e.g. determined as the diameter of the cluster or colony, respectively. In the examples herein is given suitable conditions for the transfer process. These conditions may of course be varied within appropriate limits, which is within the knowledge of a person skilled in the art.

Culturing the Blastocyst Derived Stem Cells Under Feeder Cell Free Growth Conditions in a Suitable Growth Medium and/or on a Suitable Support Substrate The presence of a suitable growth medium, such as, e.g. a tissue culture medium, and a support substrate, i.e. a growth support or coating, is very important when growing cells under feeder free conditions. When growing hBS cells on feeder cells, the feeder cells excrete various substances that promote the proliferation and inhibit the differentiation of the hBS cells. When growing cells under feeder free conditions such substances have to be supplemented to the growth medium or coated on to the surfaces of the tissue culture wells, i.e. the invention relates to a method, wherein the growth medium and/or the support substrate in step b) comprises substances that inhibits differentiation and/or promotes survival and proliferation of the blastocyst-derived stem cells. Furthermore, the cells may need some kind of coating (support medium) to be able adhere to the surfaces of e.g. the tissue culture wells, that may be used for culturing the cells.

Such substances may be added to the media. Another way of preparing a medium comprising the suitable substances for promoting proliferation and inhibiting differentiation is to culture a first population of cells in a medium, and then harvesting and filtering the medium (now denoted "conditioned medium"). The first population of cells may be cells normally used as feeder cells, such as e.g. mouse embryonic fibroblasts, human fibroblasts or cell lines derived from the same cells.

One suitable medium for the culture of hBS cells is VITROHES™-medium (Vitrolife AB, Kungsbacka, Sweden) (Serum free aqueous culture medium specifically for the propagation of undifferentiated human embryonic stem cells) supplemented with 4 ng/ml human recombinant bFGF (basic fibroblast growth factor) or alternatively a medium termed "hBS-medium" which may be comprised of; knockout Dulbecco's Modified Eagle's Medium, supplemented with 20% knockout Serum replacement and the following constituents at their respective final concentrations: 50 units/ml penicillin, 50 g/ml streptomycin, 0.1 mM non-essential amino acids, 2 mM L-glutamine, 100 M-mercaptoethanol, 4 ng/ml human recombinant bFGF (basic fibroblast growth factor).

The conditioned medium (along with anything secreted into the medium by the cells) may then be used to support the growth of a second population of cells. A suitable medium for use according to the invention, is the "k-VITROHES™-medium" or "k-hBS-medium", where a monolayer of mouse and human embryonic fibroblasts is mitomycin treated or irradiated and then incubated with "VITROHES™-medium" or "hBS-Medium" for 24 hours. The k-VITROHES™-medium or "k-BS-medium" may then be collected every day up to 3-7 times for mouse feeder and up to 3-7 times for human feeder from the same cells and sterile filtered to obtain the conditioned k-VITROBES™-medium or "k-hBS-medium". The "k-VITROHES™-medium" and "k-hBS-medium" may subsequently be stored by freezing at about −20° C. or more.

In a specific example the growth medium in step b) may be cell-free conditioned k-VITROHES™-medium or k-hBS-medium, produced by a culture of feeder cells as described in Example 3.

Another culture condition, which has been found to be favourable when growing hBS cell without feeder cells is the presence of a support substrate, i.e. the invention relates to a method, wherein step a) is performed on a support substrate. The support substrate is a surface or surface treatment on e.g. tissue culture wells, which promotes the adhesion and growth of hBS cells in an undifferentiated state, i.e. the support substrate may comprise adhesion and proliferation promoting components and components inhibiting differentiation, such as, e.g., extra cellular matrix components such as, e.g., MATRIGEL™, human extra cellular matrix (ECM) from placenta or laminin, or other components, such as, e.g. gelatine, polyornithine, fibronectin, agarose, poly-L-lysine or collagen type I.

Passaging the Blastocyst Derived Steno Cell Line Every 3-10 Days by Enzymatic and/or Mechanical Treatment In a specific embodiment of the invention, the cells are passaged. Then the cells have to be passaged every 3-10 days, such as, e.g. about every 3rd day, about every $4^{th}$ day, about every $5^{th}$ day, about every $6^{th}$ day, about every $7^{th}$ day, about every $8^{th}$ day, about every $9^{th}$ day and about every $10^{th}$ day. If the stem cell line is cultured longer than 10 days before passage, there is an increased probability that the cells undesirably will differentiate.

One way of dissociating the hBS cells is by enzymatic treatment or by using a mild chelator such as EDTA. The enzymatic treatment may be supplemented by mechanical treatment to detach the cells from the support substrate and to complete the dissociation. The enzyme used may be a collagenase, such as, e.g. collagenase IV. For the passaging the enzymatic treatment was found to be superior to mechanical treatment.

One of the other factors, which the present inventors have found may be important for the propagation of hBS cells under feeder free conditions, is the density of the cells when seeded onto the support substrate. In order to improve survival the cells may be plated at a density of 80,000-200,000 cells/cm$^2$ depending on the cell lines used. The present inventors have found that the hBS cells were stable for up to 60 passages on MATRIGEL™, still expressing the markers for undifferentiated hBS cells, even after a cycle of freezing/thawing and growth rates remained roughly comparable.

Characterization

As described above, the present invention provides a method for propagating hBS cells without feeder cells as described above, where the hBS cells maintain normal caryotype, stable proliferation rate and telomerase activity. The cells are capable of proliferating in an undifferentiated state for more than 12 months when grown under feeder free growth conditions. The hBS cells, which are cultured under feeder-free conditions, also expressed the markers associated with undifferentiated cells. Furthermore, the cells are able to develop differentiated progeny from all three germ layers upon differentiation in vitro.

Methods Used to Study hBS Cell Degree of Differentiation and Pluripotency

Immunohistochemistry

The hBS cells maintained in culture are routinely monitored regarding their state of differentiation. Cell surface markers used for monitoring the undifferentiated hBS cells are SSEA-3, SSEA-4, TRA-1-60, TRA-1-81. Human BS cells are fixed in 4% PFA and subsequently permeabilized using 0.5% Triton X-100. After washing and blocking with 10% dry milk the cells are incubated with the primary antibody. After extensive washes the cell are incubated with the secondary antibody and the nuclei are visualized by DAPI staining.

Alkaline Phosphatase

The activity of alkaline phosphatase is determined using a commercial available kit following the instructions from the manufacturer (Sigma Diagnostics).

Oct-4 RT-PCR

The mRNA levels for the transcription factor Oct-4 is measured using RT-PCR and gene specific primer sets (5'-CGTGAAGCTGGAGAAGGAGAAGCTG, 5'-CAAGGGC-CGCAGCTTACACATGTTC) and GAPDH as housekeeping gene (5'-ACCACAGTCCATGCCATCAC, 5'-TCCACCAC-CCTGTTGCTGTA).

Fluorescence In Situ Hybridization (FISH)

In one round of FISH one or more chromosomes are being selected with chromosome specific probes. This technique allows numerical genetic aberrations to be detected, if present. For this analysis a commercially available kit was used, which contains probes for chromosome 13, 18, 21 and the sex chromosomes (X and Y) (Vysis. Inc, Downers Grove, Ill., USA). For each cell line at least 200 nuclei are being analyzed. The cells are resuspended in Camoy's fixative and dropped on positively charged glass slides.

Probe LSI 13/21 is mix with LSI hybridization buffer and added to the slide and covered with a cover slip. Probe CEP X/Y/18 is mixed with CEP hybridization buffer and added in the same way to another slide. Denaturing is performed at 70° C. for 5 min followed by hybridization at 37° C. in a moist chamber for 14-20 h. Following a three step washing procedure the nuclei are stained with DAPI II and the slides analyzed in an invert microscope equipped with appropriate filters and software (CytoVision, Applied Imaging).

Karyotyping

Karyotyping allows all chromosomes to be studied in a direct way and is very informative, both numerical and larger structural aberrations can be detected. In order to detect mosaicism, at least 30 karyotypes are needed. However, this technique is both very time consuming and technically intricate. To improve the conditions for the assay the mitotic index can be raised by colcemid, a synthetic analog to colchicin and a microtubule-destabilizing agent causing the cell to arrest in metaphase, but still a large supply of cells are needed ($6 \times 10^6$ cells/analysis). The cells are incubated in the presence of 0.1 μg/ml colcemid for 1-2 h, and then washed with PBS and trypsinized. The cells are collected by centrifugation at 1500 rpm for 10 min. The cells are fixed using ethanol and glacial acetic acid and the chromosomes are visualized by using a modified Wrights staining.

Comparative Genomic Hybridization

Comparative genomic hybridization (CGH) is complementary to karyotyping. CGH gives a higher resolution of the chromosomes and is technically less challenging. Isolated DNA is nicktranslated in a mixture of DNA, A4, Texas reddUTP/FITC 12-dUTP, and DNA polymerase I. An agarose gel electrophoresis is performed to control the size of resulting DNA fragments (600-2000 bp). Test and reference DNA is precipitated and resuspended in hybridization mixture containing formamide, dextrane sulfate and SSC. Hybridization is performed on denatured glass slides with metaphases for 3 days at 37° C. in a moist chamber. After extensive washing one drop of antifade mounting mixture (VECTASHIELD®, 0.1 µg/ml DAPI II) is added and the slides covered with cover slips. Slides are subsequently evaluated under a microscope and using an image analysis system.

Telomerase Activity

Since a high activity has been defined as a criterion for hBS cells the telomerase activity is measured in the hBS cell lines. It is known that telomerase activity successively decrease when the cell reaches a more differentiated state. Quantifying the activity must therefore be related to earlier passages and control samples, and can be used as a tool for detecting differentiation. The method, Telomerase PCR ELISA kit (Roche) uses the internal activity of telomerase, amplifying the product by polymerase chain reaction (PCR) and detecting it with an enzyme linked immunosorbent assay (ELISA). The assay is performed according to the manufacturer's instructions. The results from this assay show typically a high telomerase activity (>1) for hBS cells.

Teratoma Formation in Immunodeficient Mice

One method to analyze if a human BS cell line has remained pluripotent is to xenograft the cells to immunodeficient mice in order to obtain tumors, teratomas. Various types of tissues found in the tumor should represent all three germlayers. Reports have showed various tissues in tumors derived from xenografted immunodeficient mice, such as striated muscle, cartilage and bone (mesoderm) gut (endoderm), and neural rosettes (ectoderm). Also, large portions of the tumors consist of disorganized tissue. Severe combined immunodeficient (SCID)-mice, a strain that lack B- and T-lymphocytes are used for analysis of teratoma formation. Human BS cells are surgically placed in either testis or under the kidney capsule. In testis or kidney, hBS cells are transplanted in the range of 10 000-100 000 cells. Ideally, 5-6 mice are used for each cell line at a time. Preliminary results show that female mice are more post-operative stable than male mice and that xenografting into kidney is as effective in generating tumors as in testis. Thus, a female SCID-mouse teratoma model is preferable. Tumors are usually palpable after approximate 1 month. The mice are sacrificed after 1-4 months and tumors are dissected and fixed for either paraffin- or freeze-sectioning. The tumor tissue is subsequently analyzed by immunohistochemical methods. Specific markers for all three germlayers are used. The markers currently used are: human E-Cadherin for distinction between mouse tissue and human tumour tissue, α-smooth muscle actin (mesoderm), α-Fetoprotein (endoderm), and β-III-Tubulin (ectoderm). Additionally, hematoxylin-eosin staining is performed for general morphology.

Cryopreservation and Thawing

As it appears from Example 6 herein, the hBS cells that have undergone passaging can be cryopreserved and subsequently thawed. After thawing all cell lines survived and started to grow on MATRIGEL™ coated plates in similar patterns as before cryopreservation and thawing.

Use of hBS Cells Obtained According to the Invention—Cardio-Related Diseases

The hBS cells obtained by a method according to the invention may be used in medicine.

Coronary heart disease accounts for 50% of all cardiovascular deaths and nearly 40% of the incidence of heart failure. Sudden occlusion of a major coronary artery and acute myocardial ischemia may lead to rapid death of myocytes and vascular structures. In the past, recovery of cardiac function has been fully dependent on the growth of the remaining non-infarcted portion of the ventricle. However, this is connected with a dilated myocardium, heart failure and death.

The only treatment currently available for replacing diseased myocardial tissue is organ transplantation. Because of the limited availability of donor hearts, however, relatively few potential recipients can benefit from heart transplantation. Even if the problems with cardiac availability were overcome, the high costs involved in this procedure and the radical nature of the surgery would still limit organ transplantation to only those patients with end-stage diseased hearts. Thus, alternatives to organ transplantation are needed. In a specific aspect, the present invention concerns a method for the preparation of hBS cells suitable for use as such an alternative.

Although prompt reperfusion within a narrow time window has significantly reduced early mortality from acute myocardial infarction, post-infarction heart failure resulting from ventricular remodeling is reaching epidemic proportions. Today, the only medical alternative for these patients is to undergo heart transplantation. This is a very expensive treatment being afflicted with a high immediate risk, but also with severe post-operative complications. In addition, there is today a great shortage of hearts for these types of transplantations. Instead, treatment with stem cells could be performed during acute surgery (e.g. open chest surgery), or at a later stage without surgery using e.g. balloon-catheter via the carotis artery or via systemic administration. Then time, suffering and risk for complications are reduced to a minimum. The advantage of stem cells versus organ transplantation is also the unlimited access to material since stem cells can be propagated indefinitely. Moreover, hBS cells are most certainly much less immunogenic active compared to adult hearts. Therefore, treatment of these patients with stem cells offers a time- and cost-effective treatment that also save a lot of human suffering. When stem cells transplantation to damaged myocardium becomes a clinical reality, this treatment has the potential to be the first of choice for millions of patients worldwide.

The hBS cells obtained by a method according to the invention may be used for the manufacture of a medicament for transplantation of hBS cells into a mammal for the prevention or treatment of a disease such as, e.g., a cardio-related disease including late myocardial infarction, chronic ischemic cardiomyopathy, idiopathic dilated cardiomyopathy, secondary cardiomyopathies such as, e.g. toxic, diabetic, pregnancy, amyloidosis, sarcoidosis, Fabry and haemochromatosis, end stage hypertrophic cardiomyopathy with LV dysfunction or heart failure, restrictive cardiomyopathy, end-stage hypertensive heart disease, acute myocardial infarction, angina pectoris, fulminant myocarditis, AV-block III, specific forms of congenital heart diseases in children and adults, such as, e.g., noncompaction LV, atrial and ventricular septal defects, tetralogi Fallot and other similar conditions, reconstruction of the valves and heart failure secondary to valvular disease.

The medicament for transplantation of human blastocyst-derived stem cells may be designed to be administered into the myocardium or the circulation of a mammal for the prevention or treatment of a cardio-related disease. The medicament comprises undifferentiated hBS cells or differentiated hBS cells dispersed in a pharmaceutically acceptable medium such as an aqueous medium. The medium may comprise one or more additive selected from the group consisting of pH adjusting agents, stabilizers, preservatives, osmotic pressure adjusting agent, and physiologically acceptable salts; and/or one or more agents selected from the group consisting of therapeutically active substances, prophylactically active substances, engraftment improving agents, viability improving agents, differentiation improving agent and immunosuppressive agents.

Treatment of the Cultured Cells Before Administration

The following gives a description of a suitable method for treating the cells before administration. However, the description is included for illustrative purposes and is not intended to limit the invention in any way.

The hBS cell colonies are dissociated in order to be of suitable size for transplantation and to give the cells optimal possibilities to enter and to be established in the host tissue. The colonies are partly or completely dissociated using mechanical or enzymatic treatment. The enzymatic treatment may be performed with any suitable enzyme, such as, e.g. a solution of buffered collagenase or trypsin. Any suitable collagenase may be used, such as, e.g., collagenase I, II, II, IV, V, IV etc. In the Examples is mentioned a specific example of collagenase used. Also mechanical treatment with a pipette of the cell colonies in an EDTA-solution has been found efficient. After desired sizes of the cell-aggregates are achieved, the cell solution is centrifuged, washed and the pellet dissolved in an appropriate buffer for transplantation.

Administration

The hBS-cells are administered to animals as a sterile, buffered solution of cells, or cell-colony fragments by use of different equipment and via different routes. A sufficient amount of cells are used. It is contemplated that about $10^5$-$10^8$ cells are suitable. The cells are aspirated into a sterile syringe and injected either directly into the animal or into a balloon-catheter that is placed in any of the coronary vessels. The direct injection can be directed into the cardiac tissue, to any of the cardiac cavities, or into the circulating blood. Cells can be administered with several injections at 1-3 different time points. During administration the general state of health of the animal is monitored. Moreover, the efficiency of cell transplantation in terms of leakage and cell loss is carefully followed. If needed, the animal receives other pharmaceutical or immunosuppressing treatment. A defined combination of cell transplantation and an agent improving the outcome of the treatment could be beneficial.

If appropriate, the administration of the cells may be together with one or more therapeutically or prophylactically active substance and/or together with one or more additives suitable for improving engraftment and/or viability of the hBS cells and/or one or more immunosuppressive agent. Moreover, they may be administered together with additives suitable for improving differentiation of the cells. The administration of these different agents may be before, concomitantly or after the administration of the hBS cells.

The administration of the cells may be prophylactically, acute or after some time of progress of the disease.

The invention relates also relates to a kit comprising at least a first and a second component in separate compartments. The components may comprise an agent that improves the engraftment and viability of the hBS cells, the hBS cells, one or more agents that improve differentiation of the hBS cells, and one or more pharmaceutical and/or immunosuppressing agents.

The kit may further comprise a second cell-type that improves engraftment and survival of the hBS cells.

The kit may further comprise undissociated or dissociated differentiated human BS-cell colonies.

As mentioned above, the invention also relates to the use of differentiated cells such as, e.g., cardiomyocyte-like hBS cells. Below follows a description of the development of such differentiated cells. In the following the invention is described with specific reference to cardiomyocyte-like cells. However, other cells that differentiate from hBS cells and that are suitable for use in the treatment of cardio-related disease are intended to be included in the invention as well.

Development of Differentiated Cells from hBS Cells

The hBS cell line obtained by a method as used in the present invention can be used for the preparation of differentiated cells. Therefore the invention also relates to the differentiation of hBS cells into cardiac tissue or cardiac related tissue, the cells itself and use of such cells for the preparation of medicaments for the treatment of cardio-related diseases, such as the ones mentioned above.

The hBS cells may be capable of forming cardiomyocyte-like structures, and the amount of these cells is generally higher than 10%, such as e.g. higher than 25%, or higher than 40%, or higher than 45%, or higher than 50%.

The hBS derived stem cells may have the ability to differentiate into differentiated cells, which display the expression of cardiomyocyte markers, including at least one of $\alpha$-myosin heavy chain, $\alpha$-actin, troponin I or troponin T, or one of the cardiomyocyte specific genes, including aGATA4, Mkx2.5, $\alpha$-MHC, $\beta$-MHC or ANF.

Alternatively the hBS cells have the ability to differentiate into cardiomyocyte-like cells characterized by their organization into contracting colonies, which are able to increase or decrease their frequency if $\alpha$- or $\beta$-agonists or antagonists are administered to the culturing media.

The blastocyst-derived stem cells that are capable of being made into differentiated cells may be characterised with electron microscopy and display a certain degree of myofibrillar organisation, consistent with early-stage cardiomyocytes.

In another aspect, the invention relates to the use of a preparation of differentiated cells derived from the blastocyst-derived stein cells obtained by a method according to the invention for the manufacture of a medicament for the prevention or treatment of cardio-related diseases, such as e.g., myocardial infarction, cardiomyopathy, angina pectoris and heart failure secondary to valvular disease and the diseases mentioned above.

A further object of the invention is to provide cells that may be used for the preparation of a medicament for treating and/or preventing diseases that may be cured by "cell genesis". By the term "cell genesis" is meant the generation of new cells such as cardiomyocytes, neurons, and/or different types of endothelium and vascular structures.

Treatment of the Differentiated Cells Before Administration

The differentiated cells may be treated in the same way as described above for the undifferentiated hBS cells.

Administration of Differentiated Cells

The differentiated cells may be administered in the same way as the undifferentiated hBS cells.

The invention also relates to a kit comprising at least a first and a second component in separate compartments. The components may comprise an agent that improves the engraftment and viability of the hBS cells, the hBS cells, and one or more pharmaceutical and/or immunosuppressing agents.

The kit may further comprise a second cell-type that improves engraftment and survival of the hBS cells.

The kit may further comprise undissociated or dissociated undifferentiated human BS-cell colonies.

Other Aspects of the Invention hBS cells can be used in high throughput screenings by combining high capacity with improved clinical significance. The ability to precisely modify the genome using gene targeting in hBS cells with or without differentiation of the genetically modified cells into various cell types allows the application of this technology to the identification of novel therapeutically active substances through primary and secondary screening.

Accordingly, in other aspects the invention relates to the user of the hBS cells obtained by a method according to the invention defined for i) the production of monoclonal antibodies, ii) in vitro toxicity screening, iii) in vitro screening of potential drug substances, or iv) identification of potential drug substances.

The heart is the first functional organ in the human body. Therefore the cardio-like cells and/or the pathway to obtain these cells can be used for developmental toxicity testing by intervening (i.e. adding substances with potential toxic effect) and later monitoring the development in the test compared with a control group. Accordingly, the above-mentioned aspects of the invention are of great importance.

Other embodiments of the invention appear from the appended claims. The details and particulars described above and in the claims and relating to the methods according to the invention apply mutatis mutandis to the other aspects of the invention.

The invention is further illustrated by the following figures:

FIGURE LEGENDS

FIG. 1. Blastocyst (before pronase treatment) from which human BS cell line 167 was established.

Figure 2:
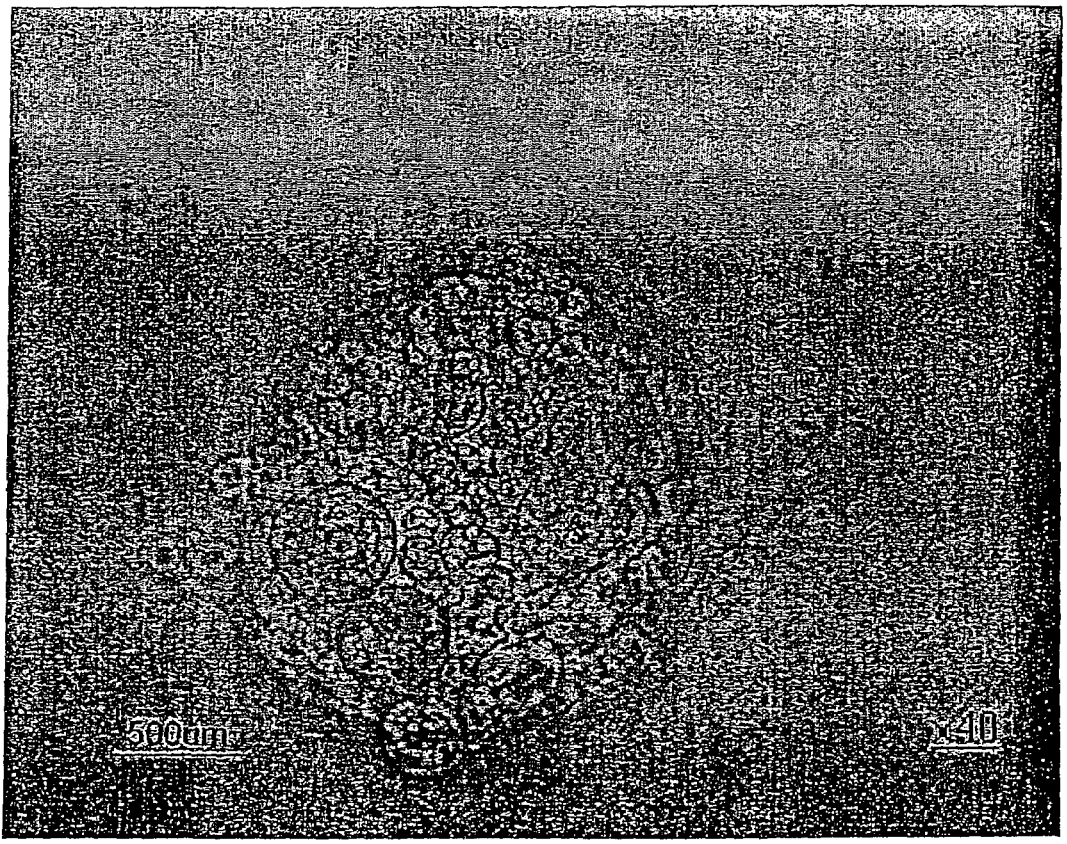

FIG. 2. Blastocyst (after pronase treatment) from which human BS cell line 167 was established.

Figure 3:
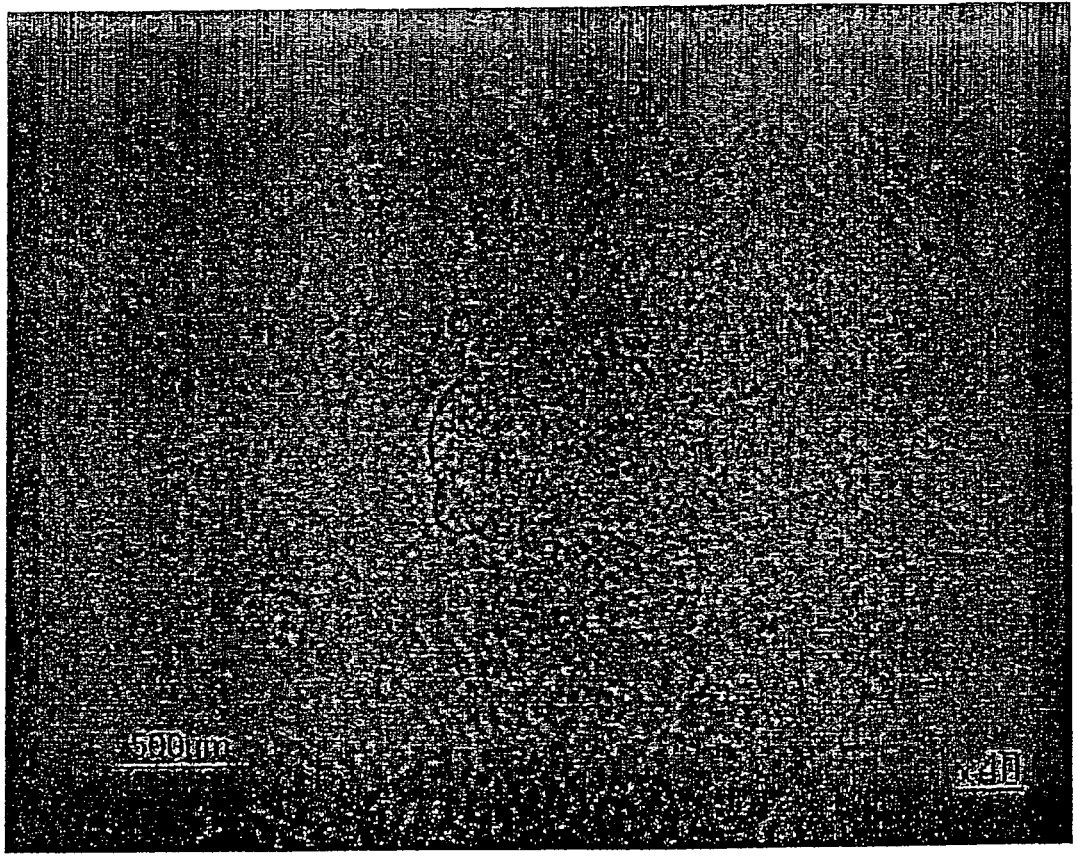

FIG. 3. Blastocyst 167 two days after plating on embryonic mouse fibroblasts.

Figure 4:
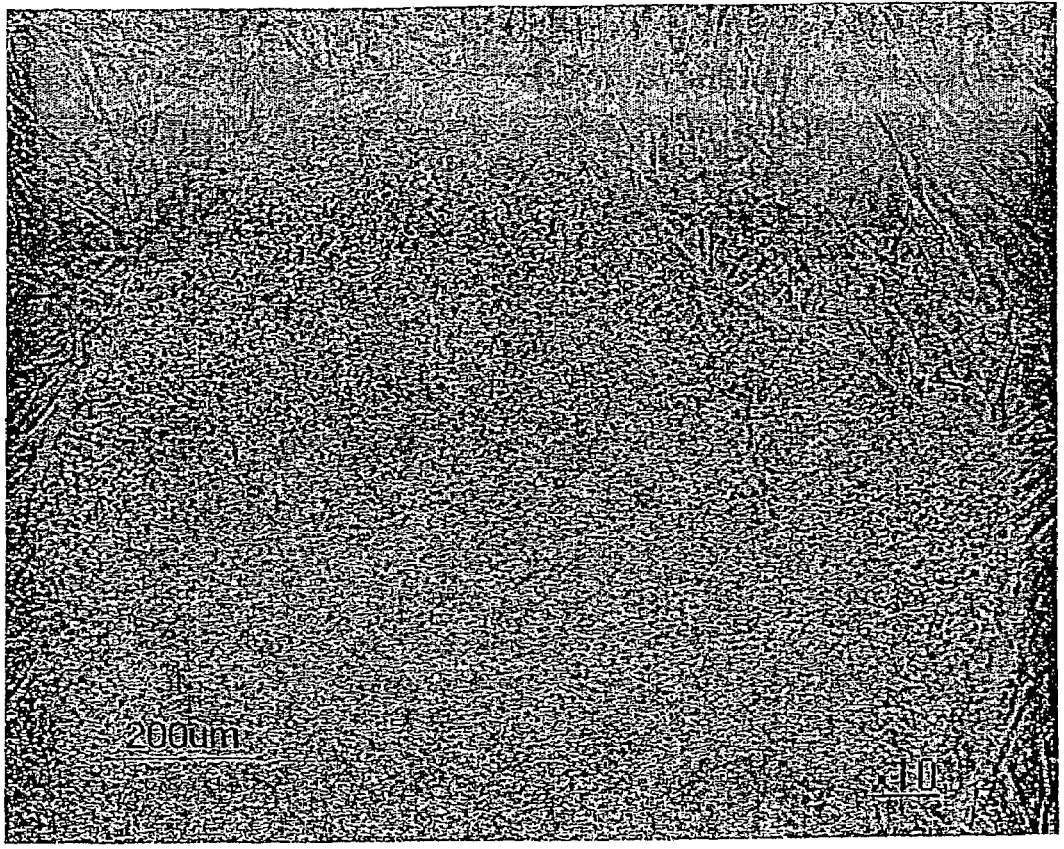

FIG. 4. Human BS cells at passage 71 cultured on embryonic mouse fibroblasts.

Figure 5:
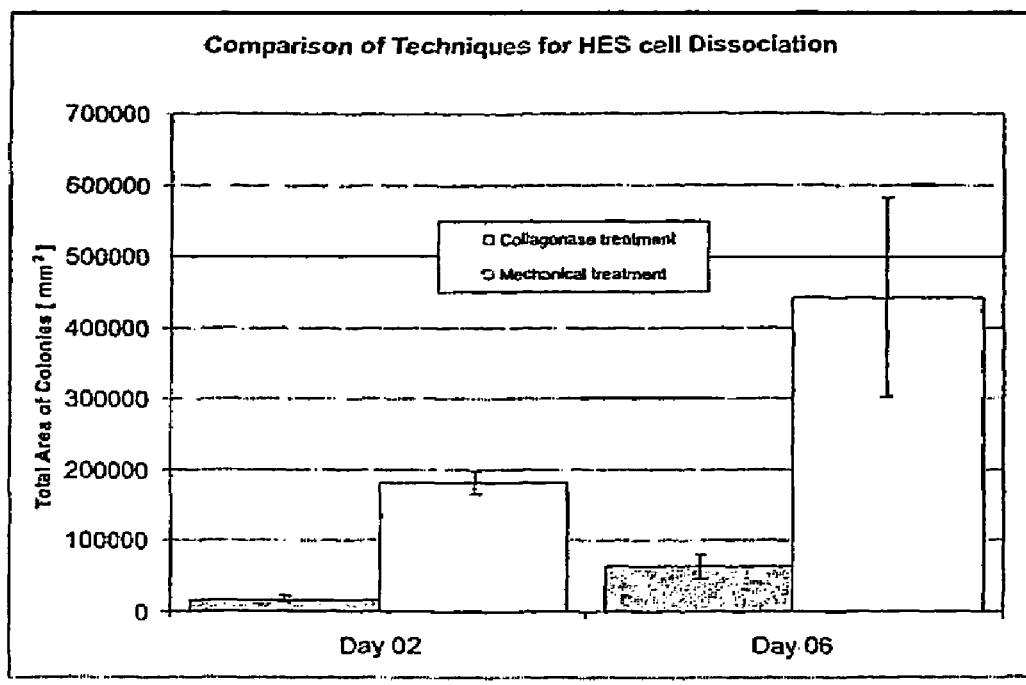

FIG. 5. A comparison chart of the two different techniques used for hES cell dissociation (Collagenase and Mechanical treatment), when establishing the cell lines on MATRIGEL™. The relative colony area ($mm^2$) was compared between the two different dissociation techniques, on day 2 and day 6 after transfer of the hES cells from mEF cultures to MATRIGEL™.

Figure 6:
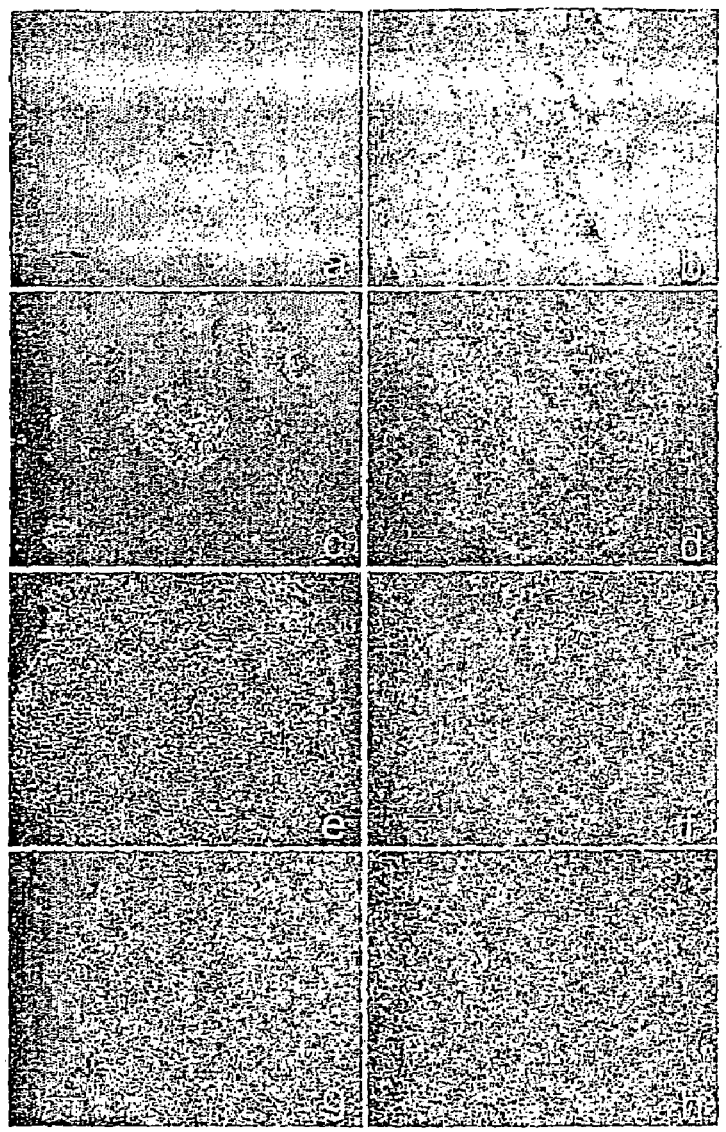

FIG. 6. Example of undifferentiated colony growth for cell line SA 167 cultured on MATRIGEL™ for (a) 2 hours, (b) 10 hours, (c) 1 day, (d) 2 days, (e) 3 days, (f) 4 days, (g) 5 days and (h) 6 days after seeding.

Figure 7:
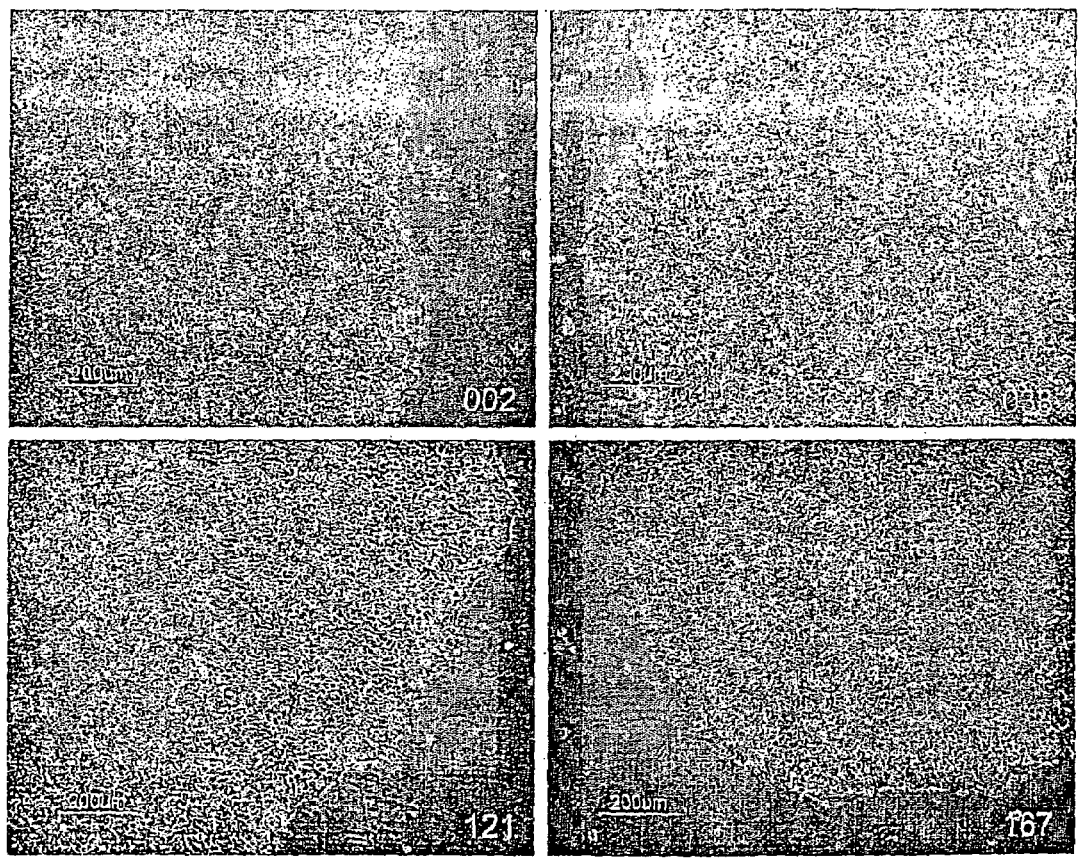

FIG. 7. Colony morphology of undifferentiated colonies of all four cell lines (SA 002, AS 038, SA 121, SA 167) cultured on MATRIGEL™ on day 4 after seeding.

Figure 8:
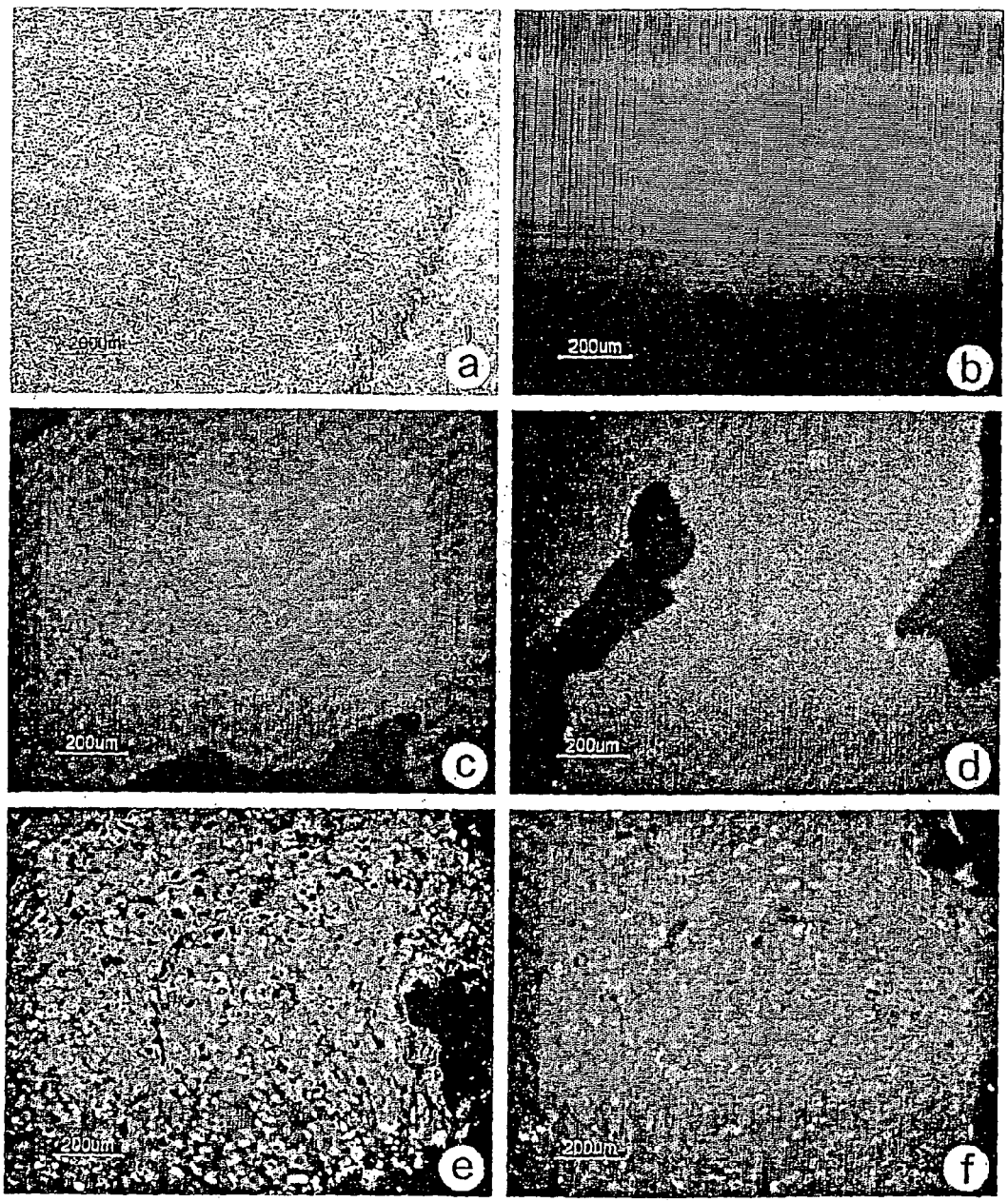

FIG. 8. Examples of staining for alkaline phosphatase (AP) activity and fluorescent immunostaining performed on the undifferentiated cell line SA167 cultured on MATRIGEL™ and after a cycle of freeze/thaw; (a) AP, (b) SSEA-1, (c) SSEA-3, (d) SSEA-4, (e) Tra-1-60, (f) Tra-1-81 staining.

Figure 9:
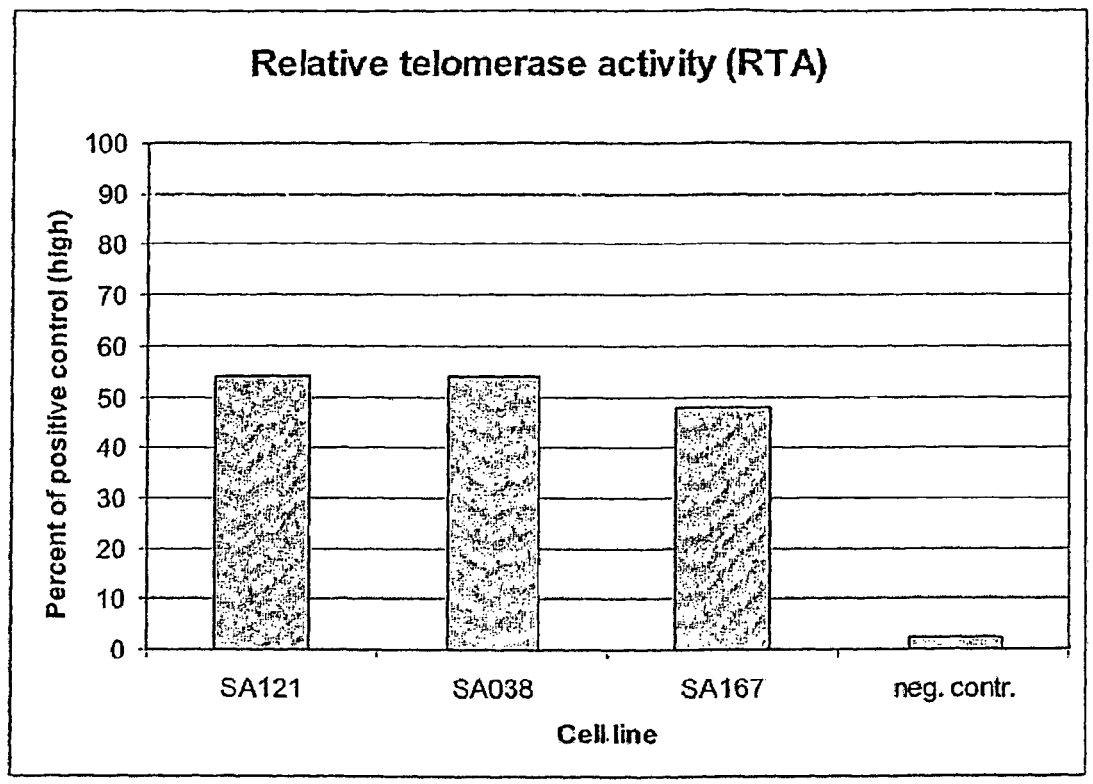

FIG. 9. The relative telomerase activity (RTA), shown for MATRIGEL™ cultures of cell line SA 121, AS 038, SA 167 and the negative control, in percentage of the positive control.

Figure 10:
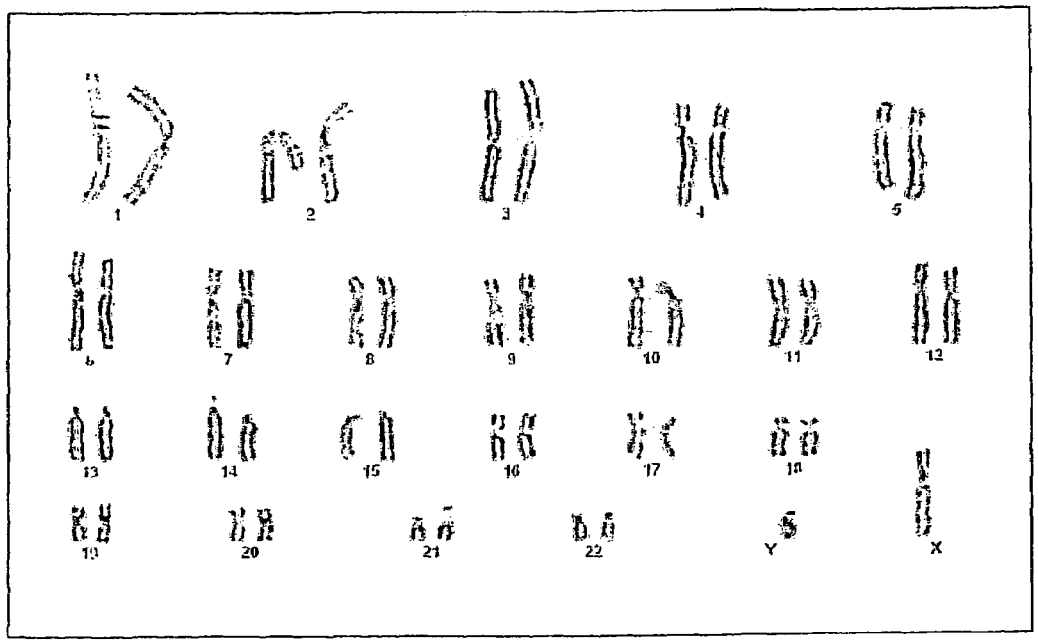

FIG. 10. Example of karyotypic analysis performed for cell line SA 121, cultured on MATRIGEL™ and after a cycle of freeze/thaw.

Figure 11:
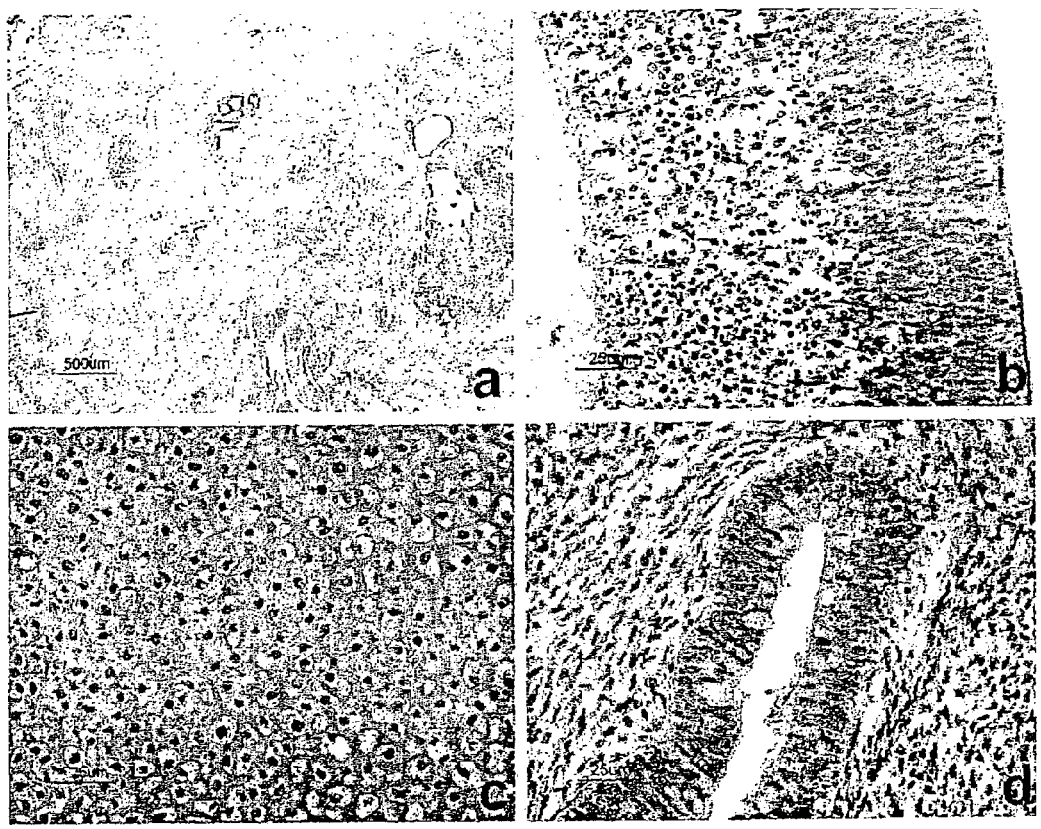

FIG. 11. Teratoma generated from MATRIGEL™ cultured cell line SA 002 after injection under the renal capsule in immunodeficient SCID mice showing; (a) teratoma overview, (b) ectoderinal differentiation, neuroectoderm, (c) mesodermal differentiation, cartilage, and (d) endodermal differentiation, columnar epithelium with numerous goblet cells.

Figure 12:
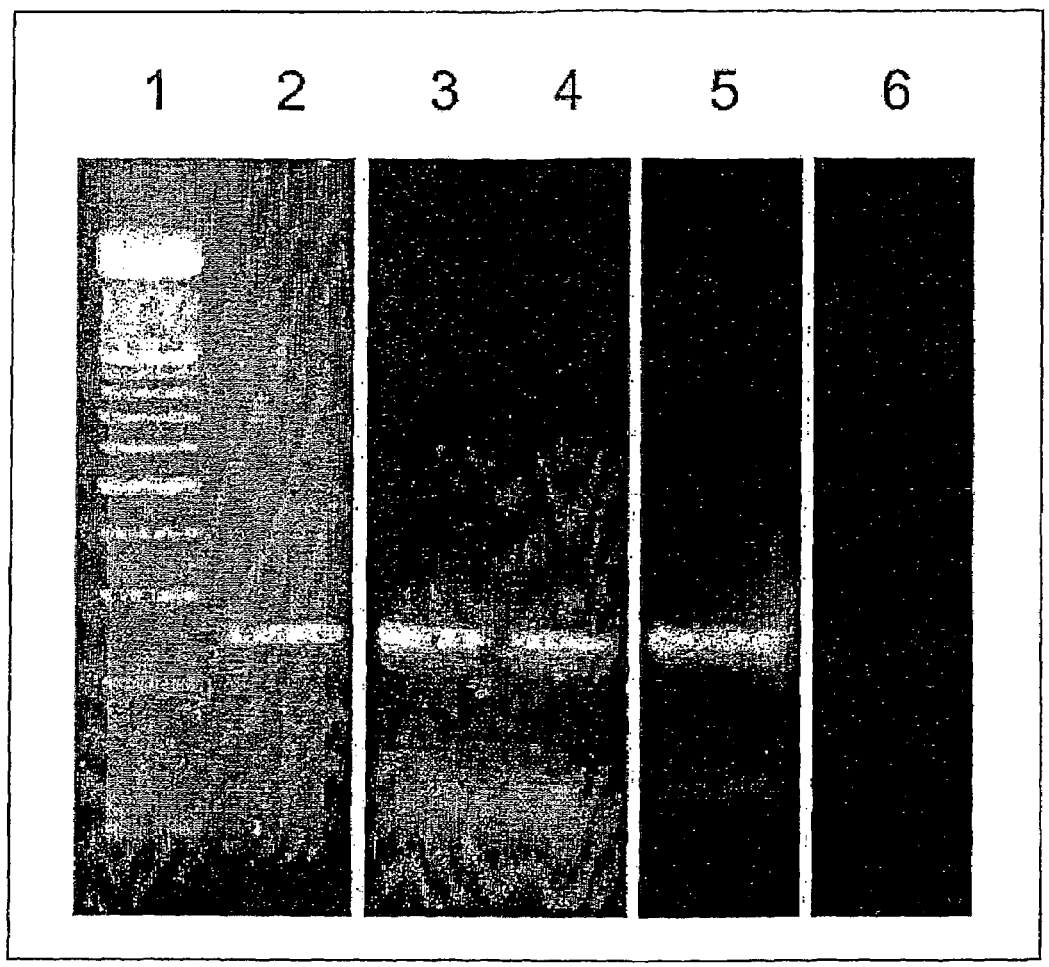

FIG. 12. RT-PCR analysis for Oct-4 expression performed for all four cell lines (SA 002, AS 038, SA 121, SA 167) after establishment on MATRIGEL™ and after a cycle of freeze/thaw. The gel is 1.5% agarose, stained with ethidium bromide. (1) 100 bp DNA ladder, (2) cell line SA 002, (3) cell line SA 121, (4) cell line SA 167, (5) cell line AS 038, and (6) negative control (water). Oct-4 PCR product is 247 bp.

FIG. 13. Percentage of cells in mitosis at day 3 of culture; a comparison between the hES cells cultured on mouse embryonic feeder layer (mEF) and on MATRIGEL™ (Cell line SA121).

Figure 14:
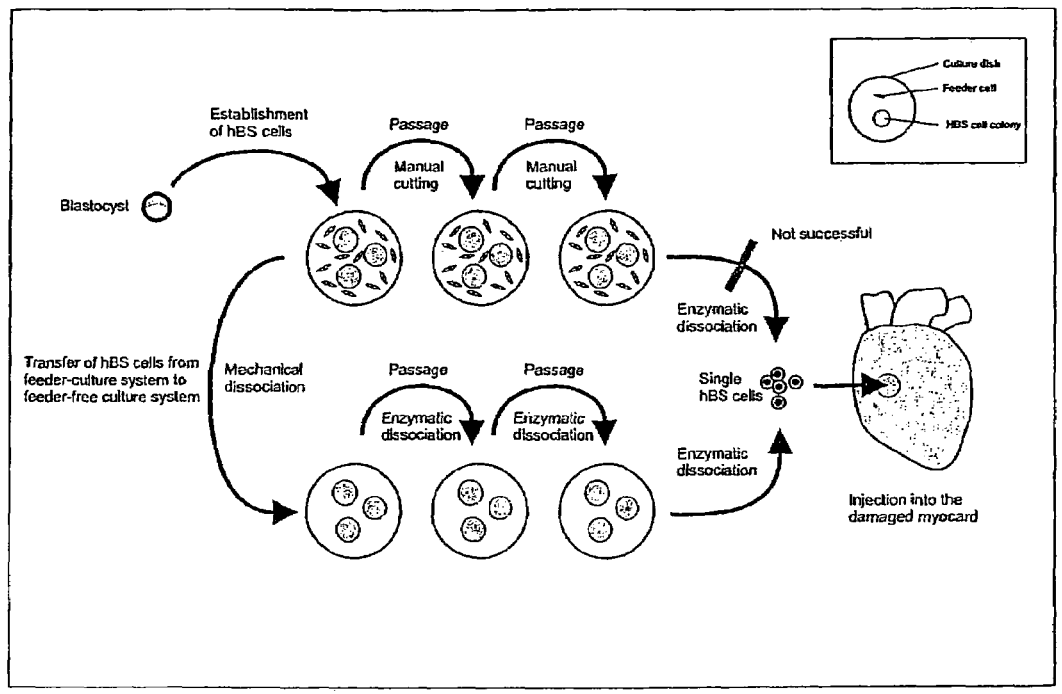

FIG. 14. Flow-chart of the hBS cell line establishment, culture on mouse feeder, transfer to feeder-free culture, culture in the feeder-free system and injection of cultured cells into the myocard.

Figure 15:
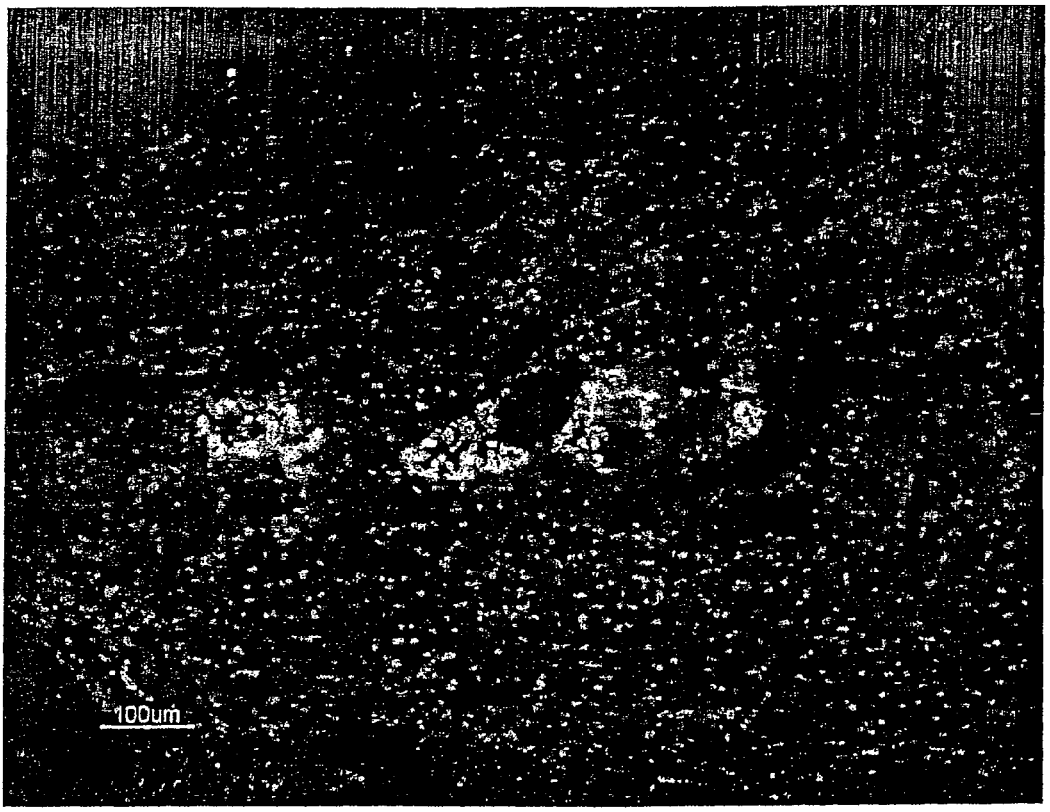

FIG. 15. Human BS cells from feeder-free culture in the rat myocard. Human cells are detected using an anti-human nuclear antigen antibody (green). Surrounding rat myocard cells are stained with the nuclear stain DAPI (blue).

REFERENCES

Gardner et al, Embryo culture systems, In Trounson, A. O., and Gardner, D. K. (eds), *Handbook of in vitro fertilization, second edition*. CRC Press, Boca Raton, pp. 205-264;

Thomson J A, Itskovitz-Eldor J, Shapiro S S et al. Embryonic stem cell lines derived from human blastocysts. Science 1998; 282:1145-1147.

Nico Heins, Mikael C. O. Englund, Cecilia Sjöblom, Ulf Dahl, Anna Tonning, Christina Berg, Anders Lindahl, Charles Hansson, and Henrik Semb; Derivation, Characterization, and Differentiation of Human Embryonic Stein Cells. Stem Cells, May 1, 2004, 22 (3)

Richards M, Fong C-Y, Chan W-K et al. Human feeders support prolonged undifferentiated growth of human inner cell masses and embryonic stem cells. Nat Biotechnol 2002; 20:933-936.

Xu C, Inokuma M S, Denham J et al. Feeder-free growth of undifferentiated human embryonic stem cells. Nat Biotechnol 2001; 19:971-974.

EXAMPLES

Example 1

Establishment of an Essentially Pure Preparation of Undifferentiated Stem Cells from Spontaneously Hatched Blastocysts Human blastocysts were derived from frozen or fresh human in vitro fertilized embryos. Spontaneously hatched blastocysts were put directly on feeder cells (EF) in VITROHES™-medium supplemented with 4 ng/ml human recombinant bFGF (basic fibroblast growth factor) and 0.125 mg/ml hyaluronic acid. After plating the blastocysts on the EF cells, growth was monitored and when the colony was large enough for manual passaging approximately 1-2 weeks after plating the inner cell mass cells were dissected from other cell types and expanded by growth on new EF cells.

Example 2

Establishment of an Essentially Pure Preparation of Undifferentiated Stem Cells from Blastocysts with an Intact Zona Pellucida For blastocysts with an intact zona pellucida (FIG. 1), a brief pronase (10 U/ml, Sigma) incubation in rS2 (TCM-2) medium (Vitrolife, Gothenburg, Sweden) was used to digest the zona (FIG. 2), after which the blastocyst was put directly on the EF cell layer in hBS medium supplemented with hyaluronic acid (0.125 mg/ml) (FIG. 3).

Example 3

Preparation of Conditioned VITROHES™-Medium (k-VITROHES™-Medium) for Feeder Free Cultures To prepare mEF cells for conditioning of VITROHES™-medium, a confluent monolayer of mEF cells (passage two) was Mitomycin C treated and seeded in a concentration of 59 000 cells/cm$^2$ in a gelatin (0.1%; Sigma) coated culture flask in Dulbecco's Modified Eagle Medium (D-MEM) supplemented with 1% Penicillin/Streptomycin (PEST; 10000 U/ml), 10% Fetal Bovine Serum (FBS) and 2 mM GLUTAMAX™-I Supplement (200 mM); all from GibcoBRL/Invitrogen, Carlsbad, Calif., USA. After a 24 hour incubation period and one wash with PBS (GibcoBRL/Invitrogen), the medium was discarded and replaced with VITROHES™-medium (0.28 ml/cm$^2$) for a 24 hour conditioning period. The conditioned VITROHES™-medium (k-VITROBES™-medium) was collected every day up to three times from the same mEF culture (in passage two) and sterile filtered by using a 0.2 µm low protein binding filter (Sarstedt, Landskrona, Sweden). The k-VITROHES™-medium was used either fresh or after freezing at –20° C. and supplemented with 4 ng/ml of bFGF (GibcoRL/Invitrogen) prior to use. The k-VITROHES™-medium may be used for up to one week if stored at +4° C. When stored at –20° C. for up to two months, no sign of reduced bioreactivity could be detected upon usage.

Example 4

Transferring of hBS Cell Lines to Feeder Free Growth Conditions

Initial hBS cell lines were maintained on Mitomycin C treated mouse feeders in 10-50 passages and cultured in VITROHES™-medium supplemented with 4 ng/ml of human basic fibroblast growth factor (bFGF) (FIG. 4).

Two different techniques were evaluated for transferring of the hBS cells from feeder culture to MATRIGEL™ coated plates, one with mechanical dissociation and one with collagenase treatment. The hBS cells were cut in square pieces, which represented the middle of the colony, by using a stem cell cutting tool (Swemed Lab AB, Billdal, Sweden), and carefully detached and transferred the cells to HBSS solution. The stem cell tool is a sterile sharpened glass capillary, with a 25 degree angle and a 200 or 300 micrometer lumen, designed for cutting, manipulation, and transfer of hBS colonies, or parts of hBS colonies. It is produced by Swemed Lab International AB, Billdal, Sweden.

Enzymatic Treatment with Collagenase (for Comparison)

After washing in HBSS the cell clusters were transferred to a Collagenase IV solution (200 U/ml; Sigma) for enzymatic dissociation. The cells were incubated for 30 minutes at 37° C. and 5% $CO_2$. During the incubation period, repeated mechanical dissociations with a pipette were performed and the dissociation process monitored in an inverted microscope. After the incubation period the cell suspension was pelleted (400 G for 5 minutes) and washed once in KnockOut™ D-MEM (GibcoBRL/Invitrogen) before being resuspended in k-VITROHES medium.

Mechanical Dissociation According to the Invention

After washing in HBSS the cell clusters were carefully dissociated mechanically by using a 1-ml automatic pipette. The dissociation process was completed when the size of the cell clusters represented approximately $\frac{1}{10}$-$\frac{1}{20}$ of the original colonies (average of 20 000 cells/original colony) corresponding to the size of cell aggregates generated by Collagenase IV treatment, as described above.

For the two different techniques, the cells were seeded into four wells each and incubated at 37° C. in 5% $CO_2$. Each experiment was repeated four times, with the same amount of cells seeded each time. After two and six days the colony size and number was calculated (FIG. 5).

Results of Example 3 and 4

To optimize the transferring of the hBS cultures from feeder to feeder-free conditions, two different techniques were evaluated; one with mechanical dissociation and one with enzymatic dissociation. Mechanical dissociation resulted in a more efficient attachment of cells to the MATRIGEL™ and a more rapid proliferation compared to the enzyme treated cultures. A significantly higher number of surviving colonies were observed two days after plating, when mechanical dissociation was compared with enzymatic dissociation (FIG. 5). The total area of all colonies generated on MATRIGEL™ after dissociation with the two different techniques, respectively, was compared ($P<0.001$). Furthermore, six days after plating the total colony area in the mechanically dissociated cultures were significantly increased compared with the enzymatically dissociated cultures ($P=0.036$) (FIG. 5).

Example 5

Culture and Passage of hBS Cells Cultured on MATRIGEL™

Four different cell lines SA 002, AS 038, SA 121 and SA 167 were used in all experiments. The cell lines were propagated on MATRIGEL™ for up to 35 passages and the morphological appearance and other hBS characteristics remained unaltered even after a cycle of freeze/thawing. All cultures consisted of well defined colonies of hBS cells without morphological signs of differentiation. After about 3-6 days the cells were passaged by taken away the medium and 1 ml of Collagenase IV (200 U/ml) solution was added to each well and incubated for 15-20 minutes. To facilitate cell detachment from the surface mechanical dissociation was performed followed by another 15 minutes of incubation. The cells were then washed, resuspended in k-VITROHES medium and seeded at a split ratio of 1:2 to 1:6 onto MATRIGEL™. The hBS cultures were passaged every 5 to 6 days and the medium was changed every second to third day.

Result of Example 5

Observations were made that during passage of the hBS cells established on MATRIGEL™, enzyme treatment with Collagenase IV was needed to detach the colonies from the surface. Enzymatic treatment during passage was also found to give an increased proliferation rate after seeding, compared to mechanical dissociation (FIG. 6, 7).

Example 6

Cryopreservation and Thawing of hBS Cells Cultured on MATRIGEL™

Four different cell lines SA 002, AS 038, SA 121 and SA 167 were treated with collagenase IV for 20-30 minutes to separate the cells from each other before freezing. After centrifugation the cells were transferred to freezing medium, which contains k-VITROHES™-medium containing 10% DMSO, 30% serum replacement and 4 ng/ml of bFGF, in a concentration of 1 million cells per ml freezing medium. The final cell suspension was a mixture of both single cells and cell clusters. The cryotubes (0.5-1.0 ml of cell suspension) were rapidly transferred to Nalgene freezing container for storages in −80° C. over night or at least for 2 hours before long-term storage in Liquid Nitrogen.

Thawing of the hBS Cells k-VITROHES™-medium has to be prepared and preheated before thawing the cells by placing the cryotubes in 37° water bath until all of the cell suspension was thawed. The cell suspension was transferred to the preheated medium for 5 minutes before centrifugation (400 G in 5 minutes). MATRIGEL™ thin layer coated (BD) wells were rehydrated by adding 1 ml of k-VITROHES™-medium to the wells and incubate 30 minutes in 37° C. The cell pellet was resuspended in k-VITROBES™-medium and transferred to either 24- or 6-well MATRIGEL™ plates.

Example 7

Characterization of Feeder Free Cultured hBS Cells

All characterization experiments were performed after establishment on MATRIGEL™ and after a cycle of freeze/thaw.

Immunocytochemistry: The cultures were passaged as described above, seeded into 6- or 24-well MATRIGEL™ plates and cultured for six days before performing the immunostaining. The cultures were washed in PBS, fixed with 4% formaldehyde (HistoLab, Gothenburg, Sweden) for 15 minutes at room temperature and then washed again three times in PBS. The monoclonal primary antibodies used were directed against SSEA-1, -3 and -4 (1:200; Developmental Studies Hybridoma Bank, University of Iowa, Iowa City, Iowa), Tra-1-60, Tra-1-81 (1:200; Santa Cruz Biotechnology, Santa Cruz, Calif.), and polyclonal rabbit anti-Phospho-Histone H3 (1:150; KeLab, Upstate). The primary antibodies were incubated over night at 4° C. before being visualized using appropriate Cy3- or FITC-conjugated secondary antibodies (1:300; Jackson ImmunoResearch Laboratories, West Grove, Pa.). Cultures were also incubated with 4'-6'Diamidino-2-phenylindole (DAPI; Sigma-Aldrich Sweden AB, Stockholm, Sweden), at a final concentration of 0.5 ug/mL, for 5 minutes at room temperature, to visualize all the cell nuclei. The stained cultures were rinsed and mounted using DAKO fluorescent mounting medium (Dakopatts AB, Älvsjö, Sweden) and visualized in an inverted fluorescent microscope (Nikon Eclipse TE2000-U). Alkaline phosphatase (AP) staining of the MATRIGEL™ cultured hBS cells was carried out according to the manufacturer's instructions using a commercially available kit (Sigma-Aldrich).

Telomerase activity: MATRIGEL™ cultured hBS cells were harvested, lysed and telomerase activity analyzed by a PCR-based ELISA (Roche Diagnostics GmbH, Mannheim, Germany) according to manufacturers instructions.

Karyotyping and FISH: The MATRIGEL™ propagated hBS cells designated for karyotyping were incubated for 1 to 3 hours in colcemid (0.1 g/ml, Invitrogen, Carlsbad, Calif., USA), dissociated, fixated, mounted on glass slides and the chromosomes visualized by using a modified Wrights staining (#WS-32, Sigma). Preparation of metaphase plates was performed as previously described. For the fluorescence in situ hybridization (FISH) analysis, a commercially available kit (MultiVysion™ PB Multicolour Probe Panel; Vysis, Inc., Downers Grove, Ill.) containing probes for chromosome 13, 18, 21 and the sex chromosomes (X and Y) was used according to the manufacturer's instructions. Slides were analyzed using an invert microscope equipped with appropriate filters and software (CytoVision, Applied Imaging, Santa Clara, Calif.).

Teratomas: For the teratoma formation experiment, immunodeficient SCID mice (C.B-17/lcrCrl-scidBR, Charles River Laboratories, Germany) were used. MATRIGEL™ propagated hBS colonies were enzymatically detached from the surface by using Collagenase IV (200 U/ml), mechanically dissociated into small cell aggregates and approximately 50 000 to 100 000 cells/organ were injected under the kidney capsule. Control animals were treated with Cryo-PBS injections or with primary brain cells from a littermate. The animals were sacrificed eight weeks after injection and the tumors were immediately fixed in a 4% solution of paraformaldehyde and paraffin embedded. For histological analysis the teratoma were sectioned to 8 μm and stained with Alcian Blue/Van Giesson.

RT-PCR analysis of Oct-4 expression: Total RNA was isolated from all four MATRIGEL™ cultured hBS cell lines by using RNeasy Mini Kit (Qiagen) according the manufacturer's instructions. The cDNA was synthesized from 1 μg of total RNA using AMV First Strand cDNA Synthesis Kit (Roche) and the PCR reaction preformed by using Platinum Taq DNA Polymerase (Invitrogen). The PCR reaction included four initial step-down cycles, with two repeated cycles for every annealing temperature, with denaturation for 15 seconds at 94° C., annealing temperature for 15 seconds at 66° to 60° C. and extension for 30 seconds at 72° C. The following cycles included 35 repeats with annealing temperature at 58° C. The forward and reverse primer sequences for Oct-4 were previously described. -actin primers were used as internal controls (sense, 5'-TGGCACCACACCTTCTA-CAATGAGC-3'; antisense, 5'-GCACAGCTTCTCCTTAAT-GTC-ACGC-3'; 400 bp product). The PCR products were size fractioned by gel electrophoresis using a 1.5% agarose gel. Human liver was used as a positive control and water as negative control for the PCR reaction.

Results of Example 6 and 7

Cell lines SA 002, AS 038, SA 121 and SA 167 were frozen and thawed by using cryopreservation techniques to see if any changes in the characterization could be found. After thawing all four cell lines survived and started to grow on MATRIGEL™ coated plates in similar pattern Pluripotency and maintenance of the four different hBS cell lines in feeder-free conditions was demonstrated and compared to previous results for feeder cultures of the respective cell lines. These characterizations were performed by examining the morphology, expression of undifferentiated markers, telomerase activity, karyotype, and differentiation in vivo.

Immunocytochemistry: SSEA-1 expression was negative in all feeder-free cultured hBS cell lines as opposed to staining with antibodies against SSEA-3, SSEA-4, TRA-1-60 and TRA 1-80 which show a clear positive immunoreaction as expected for pluripotent hBS cells. Further, the cells displayed high levels of AP reactivity (FIG. 8) in all four MATRIGEL™ propagated cell lines.

Telomerase activity: Analysis was preformed on three of the MATRIGEL™ cultured hBS cell lines (AS 038, SA 121 and SA 167). The hBS cells cultured on MATRIGEL™ were found to have high levels of telomerase activity (FIG. 9).

Karyotyping and FISH: Karyotype analysis was preformed on two of the MATRIGEL™ cultured cell lines, AS 038 and SA 121. Three of three cells from cell line AS 038 and ten of twelve cells from cell line SA 121 were found to possess normal human 46, XY karyotype (FIG. 10). The remaining two cells from the SA 121 cell line expressed an abnormal karyotype of 45, XY and 42, XY. Although, karyotypic changes seem to be normal occurring events after prolonged culturing for both feeder and feeder-free hBS cell cultures. In this study karyotypic analysis of feeder cultured hBS cells were comparable with results after MATRIGEL™ propagation, suggesting that the hBS cell karyotype remains normal and stable under these feeder-free conditions. FISH analysis was performed on two of the MATRIGEL™ propagated cell lines (SA 121 (XY) and SA 167 (XX)). Analysis was performed for chromosomes X, Y, 18, 13 and 21. For both cell lines tested at least 93% were normal. The results from the FISH analysis were comparable with results from feeder cultured hBS cell lines.

Teratoma formation: Teratoma formation was performed for two MATRIGEL™ cultured hBS cell lines, SA 167 and SA 002, and the results showed that teratomas formed consisting of differentiated cells and tissue representative from all three germ layers (endoderm, mesoderm and ectoderm (FIG. 11), providing evidence that the MATRIGEL™ propagated hBS cultures have retained their pluripotency.

Oct-4 expression: Oct-4 expression was high in all four cell lines cultured on MATRIGEL™ (FIG. 12).

Example 8

Comparison of Mitotic Index of hBS Cells Cultured Under Feeder-Free Conditions on MATRIGEL™ Coated Plates Compared to hBS Cells Cultured on Embryonic Mouse Feeder Cells Cell line SA 121 was cultured in parallel under feeder-free conditions on MATRIGEL™ coated plates and on embryonic mouse feeder cells for 3 days. The number of cells in mitosis was then quantified by nuclear immunoreactivity for phosphorylated Histone H3. The mitotic index in both cultures was calculated in order to compare the growth rate between feeder-free and feeder cultured hBS cells.

Result of Example 8

The mitotic index was similar in cultures grown under feeder-free (MATRIGEL™) compared to feeder layer conditions (FIG. 13). The doubling time for the feeder-free cultures were roughly the same (around 35 hours) as for feeder propagated hBS cells.

Example 9

Transplantation of MATRIGEL™ Cultured Cells to a Rat Heart

Human blastocyst-derived stem cell colonies prepared as described above are dissociated with a 0.5 ml collagenase-solution (Collagenase Type IV, lyophilized 179 units/mg, Gibco, Invitrogen Corporation, dissolved in HBSS to 200 U/ml), and transferred to a 15 ml tube (described in P10391 PC/P10387). The tube is centrifuged at 400×g for 5 minutes. The supernatant (collagenase solution) is discarded and the pellet is dissolved in 5 ml pre-warmed sterile HBSS (37° C.). The tube is centrifuged again at 400×g for 5 minutes. The supernatant is discarded and the pellet is dissolved in 25 µl pre-warmed sterile HBSS (37° C.). The cells are transferred to a sterile syringe and transported to the animal surgery room.

The cells were administered to the anaesthetized and ventilated rat either via 1-2 direct myocardial-injections, via injection into the left ventricle, or via systemically intravenous administration.

More detailed, male Sprague-Dawley rats ~200 g were used and MI was induced by direct cryo-injury using 3 mm probe. This procedure resulted in anterior MI engaging ~15-20% of left ventricle (LV). The hBS cells were transplanted by intramyocardial injection into the viable myocardium close to the infracted area or via systemically intravenous administration directly after cryo-injury. All animals were investigated with transthoracal echocardiography, continuous ECG and LV catheterization 1 week after transplantation.

Post-mortem, the hearts were evaluated histologically for detection and characterization of hBS cells. There were no deaths in the rats treated with hBS cells and no arrhythmias were detected either. There were no signs of abnormal tissue growth at the site of hBS cells engraftment.

The presence of human cells in the periinfarcted area was confirmed by histological analysis. The heart was excised and the tissue surrounding the injection area was dissected. This piece was frozen down in OCT solution in a freeze-container (cryomold). The whole piece was then cryosectioned in 10 µm slices using a microtome. The slices were put on microslides (plus), which were put in the freezer. Just prior to immunohistochemical analysis, the slides were thawed in room temperature, and around each heart-slice a circle was applied using an ImmEdge Pen. The samples were fixed in 4% formaldehyde, washed 5 min with PBS and 3×5 min in TBS. The slices were then incubated 30 min in room temperature with blocking agent (goat serum), followed by 24 h incubation at 37° C. with primary antibody (mouse anti-human nucleus). The slides were then washed 3×5 min in TBS, followed by incubation for 15 min in blocking solution as above. The slides were then incubated 2-3 h at 37° C. with secondary antibody (goat anti-mouse) and washed 3×5 min in TBS. All slides were then DAPI-stained for 2 min and washed 5 min in PBS. Finally, the slides were mounted in fluorescence medium (S3023, DAKO), and human cells were identified using a fluorescencemicroscope.

Results of Example 9 hBS cells for treating cardio-related diseases by administration of hBS cells were cultured in different ways. As appears from the examples herein (FIG. 15), the outcome of administration of hBS cells is dependent of how the cells are cultured. If hBS cells were cultured on MEF, few or no cells have been found. If hBS cells were cultured on MATRI-GEL™ and transplanted as in this example, a large amount of cells were identified 24 h after transplantation using the technique described above. This suggests that the MATRIGEL™ culturing technique dramatically increase the viability of the cells, or the possibility for the cells to establish in the host tissue.

Method for Establishing hBS Cells Suitable for Use in a Method of the Present Invention In PCT application published as WO 03/055992 (to the same Application) on 10 Jul. 2003, i.e. after the priority date of the present invention, a suitable method for establishing hBS cells is described. In one aspect of the present invention, the cells employed are obtained by the method claimed in WO 03/055992, which is hereby incorporated by reference.

The method for establishing pluripotent human blastocyst-derived stem cells or cell line from a fertilized oocyte comprises the steps of i) using a fertilized oocyte optionally, having a grade 1 or 2, to obtain a blastocyst, optionally having a grade A or B, ii) co-culturing the blastocyst with feeder cells for establishing one or more colonies of inner cell mass cells, iii) isolating the inner cell mass cells by mechanical dissection, iv) co-culturing of the inner cell mass cells with feeder cells to obtain a blastocyst-derived stem cell line.

v) optionally, propagation of the blastocyst-derived stem cell line.

As a starting material for this procedure, fertilized oocytes are used. The quality of the fertilized oocytes is of importance for the quality of the resulting blastocysts. The human blastocysts in step i) of the method may be derived from frozen or fresh human in vitro fertilized oocytes. In the following is described a procedure for selecting suitable oocytes for use in a method according WO 03/055992. It was found that an important success criterion for the present method is a proper selection of oocytes. Thus, if only grade 3 oocytes are applied, the probability of obtaining a hBS cell line fulfilling the general requirements (described below) is low.

Donated fresh fertilized oocytes: On day 0 the oocyte is aspirated in Asp-100 (Vitrolife), and fertilized on day 1 in IVF-50 (Vitrolife). The fertilized oocyte is evaluated based on morphology and cell division on day 3. The following scale is used for fertilized oocyte evaluation:

Grade 1 fertilized oocyte: Even blastomers, no fragments

Grade 2 fertilized oocyte: <20% fragments

Grade 3 fertilized oocyte: >20% fragments

After evaluation on day 3, fertilized oocytes of grade 1 and 2 are either implanted or frozen for storage. Fertilized oocytes of grade 3 are transferred to ICM-2 (Vitrolife). The fertilized oocytes are further cultured for 3-5 days (i.e. day 5-7 after fertilization). The blastocysts are evaluated according to the following scale:

Grade A Blastocyst: Expanded with distinct inner cell mass (ICM) on day 6

Grade B Blastocyst: Not expanded but otherwise like grade A

Grade C Blastocyst: No visible ICM

Donated frozen fertilized oocytes: At day 2 (after fertilization) the fertilized oocytes are frozen at the 4-cell stadium using Freeze-Kit (Vitrolife). Frozen fertilized oocytes are stored in liquid nitrogen. Informed consent is obtained from the donors before the 5-year limit has passed. The fertilized oocytes are thawed using Thaw-Kit (Vitrolife), and the procedure described above is followed from day 2.

As described above, fresh fertilized oocytes are from grade 3 quality, and frozen fertilized oocytes are from grade 1 and 2. According to data obtained by the establishment methods, the percentage of fresh fertilized oocytes that develop into blastocysts is 19%, while 50% of the frozed fertilized oocytes develop into blastocysts.

This means that the frozen fertilized oocytes are much better for obtaining blastocysts, probably due to the higher quality of the fertilized oocytes. 11% of the blastocysts derived from fresh fertilized oocytes develop into a stem cell line, while 15% of the blastocysts derived from frozen fertilized oocytes develop into a stem cell line. In summary, of the fertilized oocytes that were put into culture 2% of fresh fertilized oocytes developed into a stem cell line, and 7% of frozen fertilized oocytes that were put into culture developed into a stem cell line.

The culturing of the fertilized oocyte to the blastocyst-stage is performed after procedures well-known in the art. Procedures for preparing blastocysts may be found in Gardner et al, Embryo culture systems, In Trounson, A. O., and Gardner, D. K. (eds), *Handbook of in vitro fertilization, second edition*. CRC Press, Boca Raton, pp. 205-264; Gardner et al., *Fertil Steril*, 74, Suppl 3, O-086; Gardner et al, *Hunt Reprod*, 13, 3434,3440; Gardner et al, *J Reprod Immunol*, In press; and Hooper et al, *Biol Reprod*, 62, Suppl 1, 249.

After establishment of blastocysts in step i) optionally derived from fertilized oocytes having grade 1 or 2, the blastocysts having grade A or B are co-cultured with feeder cells for establishing one or more colonies of inner cell mass cells. After being plated onto feeder cells, their growth is monitored and when the colony is large enough for manual passaging (approximately 1-2 weeks after plating), the cells may be dissected from other cell types and expanded by growth on new feeder cells. The isolation of the inner cell mass cells is performed by mechanical dissection, which may be performed by using glass capillaries as a cutting tool. The detection of the inner cell mass cells is easily performed visually by microscopy and, according, it is not necessary to use any treatment of the oocytes with enzymes and/or antibodies to impair or remove the trophectodeim.

Thus, the procedure of WO 03/055992 alleviates the need for immunosurgery. By comparing the success-rate in using immunosurgery versus the present method, which leaves the trophectoderm intact, it has been observed that the much simpler, faster and non-traumatic procedure of avoiding immunosurgery is more efficient than immunosurgery. These procedures make the preparation of stem cell lines, and the differentiation of these cell lines commercially feasible. From a total of 122 blastocysts, 19 cell lines were established (15.5%). 42 blastocysts were processed by immunosurgery and 6 of these resulted in successfully established cell lines (14%). Eighty blastocysts were processed by the present method and 13 cell lines were established (16%).

Subsequent to dissection of the inner cell mass, the inner cell mass cells are co-cultured with feeder cells to obtain a blastocyst-derived stem (BS) cell line. After obtaining the hBS cell line, the cell line is optionally propagated to expand the amount of cells. Thus, the blastocyst-derived stem cell line may be propagated e.g. by passage of the stem cell line every 4-5 days. If the stem cell line is cultured longer than 4-5 days before passage, there is an increased probability that the cells undesirably will differentiate.

A specific procedure of passaging the cells in a feeder culture system is given in Establishment example 5 herein.

Human BS cell lines may be isolated either from spontaneously hatched blastocysts or from expanded blastocysts with an intact zona pellucida. In the method described above the blastocyst in step i) is a spontaneously hatched blastocyst. For hatched blastocysts the trophectodeim may be left intact. Either hatched blastocysts or blastocysts with a removed or partially removed zona pellucida may be put on inactivated feeder cells.

Zona pellucida of the blastocyst may be at least partially digested or chemically frilled prior to step ii) e.g. by treatment with one or more acidic agents such as, e.g., ZD™-10 (Vitrolife, Gothenburg, Sweden), one or more enzymes or mixture of enzymes such as pronase.

A brief pronase (Sigma) treatment of blastocysts with an intact zona pellucida results in the removal of the zona. Other types of proteases with the same or similar protease activity as pronase may also be used. The blastocysts can be plated onto said inactivated feeder cells following the pronase treatment.

In the establishment method step ii) and/or step iv) may be performed in an agent that improves the attachment of the blastocysts and/or if relevant the inner cell mass cells to the feeder cells. A suitable substance for this purpose is a hyaluronic acid.

A suitable medium for plating the blastocysts onto feeder cells can be hBS-medium that may be complemented with hyaluronic acid, which seems to promote the attachment of the blastocysts on the feeder cells and growth of the inner cell mass. Hyaluronan (HA) is an important glycosaminoglycan constituent of the extracellular matlix in joints. It appears to exert its biological effects through binding interactions with at least two cell surface receptors: CD44 and receptor for HA-mediated motility (RHAMM), and to proteins in the extracellular matrix. The positive effects of HA during the establishment of hBS cells may be exerted through its interactions with the surfactant polar heads of phospholipids in the cell membrane, to thereby stabilize the surfactant layer and thus lower the surface tension of the inner cell mass or blastocyst which may result in increased efficiency in binding to the feeder cells. Alternatively, HA may bind to its receptors on the inner cell mass or blastocyst and/or to the feeder cells and exert biological effects which positively influence the attachment and growth of the inner cell mass. According to this, other agents that may alter the surface tension of fluids, or in other ways influence the interaction between the blastocyst and feeder cells can also be used in instead of hyaluronic acid.

In the method describe above culturing of the feeder cells is of importance for the establishment of the hBS cell line. The propagation of blastocyst-derived stem cell line may comprise passage of the feeder cells at the most 3 times, such as e.g. at the most 2 times.

Suitable feeder cells for use in a method of the invention are fibroblasts of e.g. embryonic or adult origin. In a method according to the invention the feeder cells employed in steps ii) and iv) are the same or different and originate from animal source such as e.g. any mammal including human, mouse, rat, monkey, hamster, frog, rabbit etc. Feeder cells from human or mouse species are preferred.

Another important criterion for obtaining an hBS cell line fulfilling the general requirements are the conditions under which the blastocysts are cultured. The blastocyst-derived stein cell line may accordingly by propagated by culturing the stem cells with feeder cells of a density of less than about 60,000 cells per $cm^2$, such as e.g. less than about 55,000 cells per $cm^2$, or less than about 50,000 cells per $cm^2$. In a specific embodiment, the propagation of blastocyst-derived stem cell line comprises culturing the stem cells with feeder cells of a density of about 45,000 cells per $cm^2$. These values apply in those cases where mouse feeder cells are used and it is contemplated that a suitable density can be found for other types of feeder cells as well. Based on the findings of the present inventors, a person skilled in the art will be able to find such suitable densities. The feeder cells may be mitotically inactivated in order to avoid unwanted growth of the feeder cells.

The blastocyst-derived stem cell line obtained by the establishment method described above maintains selfrenewal and pluripotency for a suitable period of time and, accordingly it is stable for a suitable period of time. In the present context the term "stable" is intended to denote proliferation capacity in an undifferentiated state for more than 21 months when grown on mitotically inactivated embryonic feeder cells.

The stem cell line obtained by the establishment method described above fulfils the general requirements. Thus, the cell line i) exhibits proliferation capacity in an undifferentiated state for more than 21 months when grown on mitotically inactivated embryonic feeder cells, ii) exhibits normal euploid chromosomal karyotype, iii) maintains potential to develop into derivatives of all types of germ layers both in vitro and in vivo, iv) exhibits at least two of the following molecular markers OCT-4, alkaline phosphatase, the carbohydrate epitopes SSEA-3, SSEA-4, TRA 1-60, TRA 1-81, and the protein core of a keratin sulfate/chondroitin sulfate pericellular matrix proteinglycan recognized by the monoclonal antibody GCTM-2, v) does not exhibit molecular marker SSEA-1 or other differentiation markers, vi) retains its pluripotency and forms teratomas in vivo when injected into immuno-compromised mice, vii) is capable of differentiating.

The undifferentiated hBS cells obtained by the method described above are defined by the following criteria; they were isolated from human pre-implantation fertilized oocytes, i.e. blastocysts, and exhibit a proliferation capacity in an undifferentiated state when grown on mitotically inactivated feeder cells; they exhibit a normal chromosomal karyotype; they express typical markers for undifferentiated hBS cells, e.g. OCT-4, alkaline phosphatase, the carbohydrate epitopes SSEA-3, SSEA-4, TRA 1-60, TRA 1-81, and the protein core of a keratin sulfate/chondroitin sulfate pericellular matrix proteinglycan recognized by the monoclonal antibody GCTM-2, and do not show any expression of the carbohydrate epitope SSEA-1 or other differentiation markers. Furthermore, pluripotency tests in vitro and in vivo (teratomas) demonstrate differentiation into derivatives of all gem layers.

According to the above, the method proveds an essentially pure preparation of pluripotent human BS cells, which i) exhibits proliferation capacity in an undifferentiated state for more than 21 months when grown on mitotically inactivated embryonic feeder cells; ii) exhibits normal euploid chromosomal karyotype; iii) maintains potential to develop into derivatives of all types of germ layers both in vitro and in vivo; iv) exhibits at least two of the following molecular markers OCT-4, alkaline phosphatase, the carbohydrate epitopes SSEA-3, SSEA-4, TRA 1-60, TRA 1-81, and the protein core of a keratin sulfate/chondroitin sulfate pericellular matrix proteinglycan recognized by the monoclonal antibody GCTM-2 v) does not exhibit molecular marker SSEA-1 or other differentiation markers, and vi) retains its pluripotency and forms teratomas in vivo when injected into immunocompromised mice, and vii) is capable of differentiating.

Procedures for the detection of cell markers can be found in Gage, F. H., Science, 287:1433-1438 (2000) and are also described above.

The establishment method is described below in the following "establishment examples". These examples are included herein for illustrative purposes only and are not intended to limit the scope of the invention in any way. The general methods described herein are well known to a person skilled in the art and all reagents and buffers are readily available, either commercially or easily prepared according to well-established protocols in the hands of a person skilled in the art. All incubations were in 37° C., under a $CO_2$ atmosphere.

One suitable medium used is termed "BS-cell medium" or "BS-medium" and may be comprised of; knockout Dulbecco's Modified Eagle's Medium, supplemented with 20% knockout Serum replacement and the following constituents at their respective final concentrations: 50 units/ml penicillin, 50 g/ml streptomycin, 0.1 mM non-essential amino acids, 2 mM L-glutamine, 100 M-mercaptoethanol, 4 ng/ml human recombinant bFGF (basic fibroblast growth factor).

Another suitable medium is "BS cell body medium", this may be comprised as follows; knockout Dulbecco's Modified Eagle's Medium, supplemented with 20% knockout Serum replacement and the following constituents at their respective final concentrations: 50 units/ml penicillin, 50 g/ml streptomycin, 0.1 mM non-essential amino acids, 2 mM L-glutamine and 100 M-mercaptoethanol.

In the present context the term "stable" is intended to denote proliferation capacity in an undifferentiated state for more than 21 months when grown on mitotically inactivated embryonic feeder cells.

ESTABLISHMENT EXAMPLES

Establishment Example 1

Establishment of an Essentially Pure Preparation of Undifferentiated Stem Cells from Spontaneously Hatched Blastocysts Human blastocysts were derived from frozen or fresh human in vitro fertilized embryos. Spontaneously hatched blastocysts were put directly on feeder cells (EF) in hBS cell medium (KNOCKOUT Dulbecco's Modified Eagle's Medium, supplemented with 20% KNOCKOUT Serum replacement, and the following constituents at the final concentrations: 50 units/ml penicillin, 50 g/ml streptomycin, 0.1 mM non-essential amino acids, 2 mM L-glutamine, 100 M-mercaptoethanol, 4 ng/ml human recombinant bFGF (basic fibroblast growth factor), supplemented with 0.125 mg/ml hyaluronic acid. After plating the blastocysts on the EF cells, growth was monitored and when the colony was large enough for manual passaging approximately 1-2 weeks after plating) the inner cell mass cells were dissected from other cell types and expanded by growth on new EF cells.

Establishment Example 2

Establishment of an Essentially Pure Preparation of Undifferentiated Stem Cells from Blastocysts with an Intact Zona Pellucida For blastocysts with an intact zona pellucida, a brief pronase (10 U/ml, Sigma) incubation in rS2 (ICM-2) medium (Vitrolife, Gothenburg, Sweden) was used to digest the zona, after which the blastocyst was put directly on the EF cell layer in hBS medium supplemented with hyaluronic acid (0.125 mg/ml).

Establishment Example 3

Histo-Chemical Staining for Alkaline Phosphatase

The cells were harvested for RT-PCR and histological (alkaline phosphatase) and immunocytochemical analysis (see below). RNA isolation and RT-PCR. Total cellular RNA was prepared using Rneasy Mini Kit (Qiagen) according to the manufacturer's recommendations. The cDNA synthesis was carried out using AMV First Strand cDNA Synthesis Kit for RT-PCR (Roche) and PCR using Platinum Taq DNA Polymerase (Invitrogen). Histochemical staining for alkaline phosphatase was carried out using commercially available kit (Sigma) following the manufacturer's recommendations.

Establishment Example 4

Preparation and Culturing of hBS Cell Line

Mouse embryonic fibroblasts feeder cells were cultivated on tissue culture dishes in EMFI-medium: DMEM (Dulbecco's Modified Eagle's Medium), supplemented with 10% FCS (Fetal Calf Serum), 0.1 M-mercaptoehanol, 50 units/ml penicillin, 50 g/ml streptomycin and 2 mM L-glutamine (GibcoBRL). The feeder cells were mitotically inactivated with Mitomycin C (10 g/ml, 3 hrs). Human BS cell-colonies were expanded by manual dissection onto inactivated mouse embryonic fibroblasts feeder cells.

Human BS cells were cultured on mitotically inactivated mouse embryonic fibroblasts feeder cells in tissue culture dishes with hBS-cell medium: knockout Dulbecco's Modified Eagle's Medium, supplemented with 20% knockout Serum replacement and the following constituents at their respective final concentrations: 50 units/ml penicillin, 50 g/ml streptomycin, 0.1 mM non-essential amino acids, 2 mM L-glutamine, 100 M-mercaptoethanol, 4 ng/ml human recombinant bFGF (basic fibroblast growth factor). Seven days after passage the colonies were large enough to generate hBS cell bodies.

hBS cell colonies were cut with glass capillaries into 0.4× 0.4 mm pieces and plated on non-adherent bacterial culture dishes containing hBS cell body medium: knockout Dulbecco's Modified Eagle's Medium, supplemented with 20% knockout Serum replacement and the following constituents at their respective final concentrations: 50 units/ml penicillin, 50 g/ml streptomycin, 0.1 mM non-essential amino acids, 2 mM L-glutamine and 100M-mercaptoethanol. The hBS cell bodies, including cystic hBS cell bodies, formed over a 7-9-day period.

Establishment Example 5

Passage of hBS Cells

Before passage the hBS cells are photographed using a Nikon Eclipse TE2000-U inverted microscope (10× objective) and a DXM 1200 digital camera. Colonies are passaged every 4-5 days. The colonies are big enough to be passaged when they can be cut in pieces (0.1-0.3×0.1-0.3 mm). The first time the cells are passaged, they have grown for 1-2 weeks and can be cut in approximately four pieces.

The colonies are focused, one by one, in a stereo-microscope and cut in a checkered pattern according to the size above. Only the inner homogeneous structure is passaged. Each square of the colony is removed with the knife, aspirated into a capillary and placed on new feeder cells (with the maximum age of 4 days). 10-16 squares are placed evenly in every new IVF-dish. The dishes are left five to ten minutes so the cells can adhere to the new feeder and then placed in an incubator. The hBS medium is changed three times a week. If the colonies are passaged, medium is changed twice that particular week. Normally a "half change" is made, which means that only half the medium is aspirated and replaced with the equal amount of fresh, tempered medium. If necessary the entire volume of medium can be changed.

Establishment Example 6

Vitrification of hBS Cells

Colonies with the appropriate undifferentiated morphology from the cell line are cut as for passage. 100-200 ml liquid nitrogen is sterile filtered into a sufficient amount of cryotubes. Two solutions A and B are prepared (A: 800 @1 Cryo PBS with 1M Trehalose, 100 @1 etylen glycole and 100 @1 DMSO, B: 600 @1 Cryo PBS with 1M Trehalose, 200 @1 etylen glycole and 200 @1 DMSO) and the colonies are placed in A for 1 minute and in B for 25 seconds. Closed straws are used to store the frozen colonies. After the colonies have been transferred to a straw, it is immediately placed in a cryotube with sterile filtered nitrogen.

Establishment Example 7

Seeding of Embryonic Mouse Feeder (EMFi) Cells

The cells are inactivated with EMFi medium containing Mitomycin C by incubation at 37° C. for 3 hours. IVF-dishes are coated with gelatin. The medium is aspirated and the cells washed with PBS. PBS is replaced with trypsin to detach the cells. After incubation, the trypsin activity is stopped with EMFi medium. The cells are then collected by centrifugation, diluted 1:5 in EMFi medium, and counted in a Bürker chamber. The cells are diluted to a final concentration of 170K cells/ml EMFi medium. The gelatin in the IVF-dishes is replaced with 1 ml cell suspension and placed in an incubator. EMFi medium is changed the day after the seeding.

The invention claimed is:

1. A method for transferring human blastocyst-derived stem cells (hBS cells) into a feeder-free culture system, the method comprising the steps of:
   a) mechanically dissociating without an enzymatic treatment hBS cells grown on a feeder cell layer;
   b) transferring the mechanically dissociated hBS cells to a feeder cell free culture; and
   c) culturing the hBS cells under feeder-free growth conditions in a suitable growth medium and on a suitable support substrate, wherein said suitable growth medium is a cell-free medium conditioned by previous exposure to feeder cells, and said suitable support substrate comprises a cell-free matrix comprising extracellular matrix proteins.

2. The method of claim 1, further comprising the step of:
   d) following step c), passaging the hBS cells every 3-10 days by mechanical and/or enzymatic treatment.

3. The method of claim 1, wherein the mechanical dissociation in step a) is performed by dissection of the hBS cells by means of a suitable cutting tool.

4. The method of claim 3, wherein step a) comprises cutting pieces from the center of a colony of hBS cells grown on a feeder cell layer and step b) comprises transferring the pieces to a feeder cell free culture as cell clusters.

5. The method of claim 4, wherein the cell clusters are dissected mechanically one or more times prior to transferring the cell clusters to the feeder free culture.

6. The method of claim 5, wherein the mechanical dissection is performed until the cell clusters have a size that is at least 50% of that of the original colony.

7. The method of claim 6, wherein the size is determined as the diameter of the cluster or colony, respectively.

8. The method of claim 1, wherein said support substrate further comprises a component that inhibits differentiation and/or promotes survival and proliferation and/or adhesion of the hBS cells of step c).

9. The method of claim 1, wherein said growth medium further comprises factors that inhibit differentiation and/or promote survival and proliferation of the hBS cells of step b).

10. The method of claim 1, wherein the hBS cells of step c):
   i) exhibit proliferation capacity in an undifferentiated state for more than 12 months when grown under feeder free growth conditions,
   ii) exhibit normal euploid chromosomal karyotype,
   iii) maintain potential to develop into derivatives of all types of germ layers both in vitro and in vivo,
   iv) exhibit at least two of the following markers OCT-4, alkaline phosphatase, the carbohydrate epitopes SSEA-3, SSEA-4, TRA 1-60, TRA 1-81, and the protein core of a keratin sulfate/chondroitin sulfate pericellular matrix proteinglycan recognized by the monoclonal antibody GCTM-2,
   v) do not exhibit marker SSEA-1 or other differentiation markers,
   vi) retain its pluripotency and forms teratomas in vivo when injected into immuno-compromised mice, and
   vii) are capable of differentiation.

11. The method of claim 2, wherein the hBS cells of step d) have the ability to differentiate into cells which express at least one cardiomyocyte marker and/or at least one cardiomyocyte-specific gene.

12. The method of claim 11, wherein the at least one cardiomyocyte marker is selected from the group consisting of α-myosin heavy chain, α-actin, troponin I, and troponin II; and wherein the at least one cardiomyocyte-specific gene is selected from the group consisting of GATA4, Mkx2.5, α-MHC, β-MHC and ANF.

13. The method of claim 11, wherein the cells which express at least one cardiomyocyte marker and/or at least one cardiomyocyte-specific gene form contracting colonies, which are able to increase or decrease their frequency when a or B agonists or antagonists are administered to the culturing media.

14. The method of claim 11, wherein the amount of cells which express at least one cardiomyocyte marker and/or at least one cardiomyocyte-specific gene is higher than 25% of the total amount of the cells within the culture.

15. The method of claim 2, wherein step d) comprises passaging the hBS cells in feeder-free culture every 3-10 days by mechanical treatment.

16. The method of claim 15, wherein the enzyme is a collagenase.

17. The method of claim 16, wherein the collagenase is collagenase IV.

18. The method of claim 15, wherein step d) comprises dissociation of the hBS cells by subjecting the hBS cells to an EDTA solution.

19. The method of claim 18, wherein the concentration of the EDTA solution is at the most about 100 mM.

20. The method of claim 19, wherein the concentration of the EDTA solution is selected from the following group of concentrations: from about 0.1 to about 100 mM, from about 0.2 to about 75 mM, from about 0.3 to about 50 mM, from about 0.4 to about 25 mM, about 20 mM or less, about 15 mM or less, about 10 mM or less, about 5 mM or less, about 1 mM or less, and about 0.5 mM or less.

* * * * *

UNITED STATES PATENT AND TRADEMARK OFFICE
CERTIFICATE OF CORRECTION

PATENT NO. : 7,638,328 B2
APPLICATION NO. : 10/555694
DATED : December 29, 2009
INVENTOR(S) : Eriksson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this

Ninth Day of November, 2010

David J. Kappos
*Director of the United States Patent and Trademark Office*